US007641780B2

(12) United States Patent (10) Patent No.: US 7,641,780 B2
Lee et al. (45) Date of Patent: *Jan. 5, 2010

(54) TWO-DIMENSIONAL MICROFLUIDICS FOR PROTEIN SEPARATIONS AND GENE ANALYSIS

(75) Inventors: Cheng Sheng Lee, Ellicott City, MD (US); Don DeVoe, Bethesda, MD (US)

(73) Assignees: Calibrant Biosystems, Inc., Rockville, MD (US); The University of Maryland, Riverdale, MD (US)

( * ) Notice: Subject to any disclaimer, the term of this patent is extended or adjusted under 35 U.S.C. 154(b) by 1025 days.

This patent is subject to a terminal disclaimer.

(21) Appl. No.: 11/086,400

(22) Filed: Mar. 23, 2005

(65) Prior Publication Data
US 2006/0054504 A1 Mar. 16, 2006

Related U.S. Application Data

(63) Continuation-in-part of application No. 10/135,385, filed on May 1, 2002, now Pat. No. 6,929,730, application No. 11/086,400, which is a continuation-in-part of application No. 10/135,386, filed on May 1, 2002, now Pat. No. 6,974,526.

(60) Provisional application No. 60/287,801, filed on May 1, 2001, provisional application No. 60/287,754, filed on May 1, 2001.

(51) Int. Cl.
*G01N 27/453* (2006.01)
*G01N 30/02* (2006.01)
*B01L 3/00* (2006.01)

(52) U.S. Cl. ............................. 204/601; 422/70; 422/99

(58) Field of Classification Search ......... 204/601–605, 204/451–455; 422/70, 99, 100, 50
See application file for complete search history.

(56) References Cited

U.S. PATENT DOCUMENTS 4,576,702 A 3/1986 Peck et al. .................. 204/299

(Continued)

FOREIGN PATENT DOCUMENTS

WO WO 94 28406 12/1994

(Continued)

OTHER PUBLICATIONS

CAL001—Hillenkamp et al., "Matrix-Assisted Laser Desorption/Ionization Mass Spectrometry of Biopolymers", *Analytical Chemistry*, vol. 63, No. 24, Dec. 15, 1991, pp. 1193A-1202A.

(Continued)

*Primary Examiner*—Alex Noguerola
(74) *Attorney, Agent, or Firm*—Pillsbury Winthrop Shaw Pittman LLP

(57) ABSTRACT

The invention provides a microfluidic apparatus for performing 2-D biomolecular separations. The microfluidic 2-D device may include first and second planar substrates which include at least a first dimension microchannel extending in a first direction and an array of second dimension microchannels extending in a second direction, preferably, orthogonal to the first dimension. The ends of at least some of the microchannels are in fluid communication with a plurality of reservoirs. The substrates may further include a number of microchannels and reservoirs. The reservoirs are in electrical communication with a plurality of electrodes and voltage power sources. The device enables two dimensional separations of proteins, DNA and other biomolecules. According to another aspect of the invention, an array of tertiary microchannels extending in a third direction may be utilized.

18 Claims, 13 Drawing Sheets

U.S. PATENT DOCUMENTS

| | | | | |
|---|---|---|---|---|
| 4,708,782 | A | 11/1987 | Andresen et al. | 204/299 R |
| 5,066,377 | A | 11/1991 | Rosenbaum et al. | 204/182.8 |
| 5,102,518 | A | 4/1992 | Doering et al. | 204/180.1 |
| 5,131,998 | A | 7/1992 | Jorgenson et al. | 204/299 R |
| 5,217,591 | A | 6/1993 | Gombocz et al. | 204/299 |
| 5,240,577 | A | 8/1993 | Jorgenson et al. | 204/180.1 |
| 5,245,185 | A | 9/1993 | Busch et al. | 250/288 |
| 5,269,900 | A | 12/1993 | Jorgenson et al. | 204/299 R |
| 5,275,710 | A | 1/1994 | Gombocz et al. | 204/299 |
| 5,316,630 | A | 5/1994 | Dasgupta | 204/180 |
| 5,389,221 | A | 2/1995 | Jorgenson et al. | 204/209 R |
| 5,496,460 | A | 3/1996 | Jorgenson et al. | 204/604 |
| 5,505,831 | A | 4/1996 | Liao et al. | 204/451 |
| 5,541,420 | A | 7/1996 | Kambara | 204/602 |
| 5,569,365 | A | 10/1996 | Rabin et al. | 204/450 |
| 5,587,062 | A | 12/1996 | Togawa et al. | 204/613 |
| 5,599,432 | A | 2/1997 | Manz et al. | 204/451 |
| 5,635,045 | A | 6/1997 | Alam | 204/462 |
| 5,795,720 | A | 8/1998 | Henco et al. | 435/6 |
| 5,916,428 | A | 6/1999 | Kane et al. | 204/601 |
| 5,957,579 | A | 9/1999 | Kopf-Sill et al. | 366/340 |
| 6,013,165 | A | 1/2000 | Wiktorowicz et al. | 204/456 |
| 6,068,752 | A | 5/2000 | Dubrow et al. | 204/604 |
| 6,068,767 | A | 5/2000 | Garguilo et al. | 210/198.2 |
| 6,167,910 | B1 | 1/2001 | Chow | 137/827 |
| 6,186,660 | B1 | 2/2001 | Kopf-Sill et al. | 366/340 |
| 6,235,175 | B1 | 5/2001 | Dubrow et al. | 204/453 |
| 6,251,343 | B1 | 6/2001 | Dubrow et al. | 422/102 |
| 6,274,089 | B1 | 8/2001 | Chow et al. | 422/101 |
| 6,358,387 | B1 | 3/2002 | Kopf-Sill et al. | 204/603 |
| 6,406,604 | B1 | 6/2002 | Guzman | 204/601 |
| 6,537,432 | B1 | 3/2003 | Schneider et al. | 204/450 |
| 6,540,896 | B1 | 4/2003 | Manz et al. | 204/451 |
| 6,592,735 | B1 | 7/2003 | Meier et al. | 204/621 |
| 6,776,911 | B2 | 8/2004 | Citterio et al. | 210/635 |
| 6,818,112 | B2 | 11/2004 | Schneider et al. | 204/450 |
| 6,929,730 | B2 * | 8/2005 | Lee et al. | 204/451 |
| 6,969,452 | B2 | 11/2005 | He et al. | 204/451 |
| 6,974,526 | B2 * | 12/2005 | Lee et al. | 204/451 |
| 7,473,532 | B2 | 1/2009 | Darfler et al. | 435/7.2 |
| 2002/0033336 | A1 | 3/2002 | Liu et al. | 204/450 |
| 2002/0106700 | A1 | 8/2002 | Foote et al. | 435/7.5 |
| 2003/0013203 | A1 | 1/2003 | Jedrzejewski et al. | 436/102 |
| 2003/0089605 | A1 | 5/2003 | Timperman | 204/450 |
| 2003/0106797 | A1 | 6/2003 | Schneider et al. | 204/452 |
| 2004/0195099 | A1 | 10/2004 | Jacobson et al. | 204/450 |
| 2005/0155861 | A1 | 7/2005 | Guzman | 204/451 |
| 2005/0217996 | A1 | 10/2005 | Liu et al. | 204/603 |
| 2005/0269267 | A1 | 12/2005 | Patton et al. | 210/656 |
| 2006/0071665 | A1 | 4/2006 | Blake et al. | 324/464 |
| 2006/0083753 | A1 | 4/2006 | Straub et al. | 424/190.1 |
| 2006/0086611 | A1 | 4/2006 | Curcio | 204/451 |
| 2006/0275801 | A1 | 12/2006 | Henkin | 435/6 |

FOREIGN PATENT DOCUMENTS

| | | |
|---|---|---|
| WO | WO 98/00231 | 1/1998 |
| WO | WO 00/57170 | 9/2000 |

OTHER PUBLICATIONS

CAL002—Fenselau, "MALDI-MS and Strategies for Protein Analysis", *Analytical Chemistry News & Features*, vol. 69, Nov. 1, 1997, pp. 661A-665A.

CAL003—Kebarle et al., "From Ions in Solution to Ions in the Gas Phase—The Mechanism of Electrospray Mass Spectrometry", *Analytical Chemistry*, vol. 65, No. 22, Nov. 15, 1993, pp. 972A-986A.

CAL004—Yates, III, "Special Feature: Tutorial: Mass Spectrometry and the Age of the Proteome", *Journal of Mass Spectrometry*, vol. 33, 1998, pp. 1-19.

CAL005—Klose et al., "Two-Dimensional Electrophoresis of Proteins: An Updated Protocol and Implications for a Functional Analysis of the Genome", *Electrophoresis*, vol. 16, 1995, pp. 1034-1059.

CAL006—Jungblut et al., "Resolution Power of Two-Dimensional Electrophoresis and Identification of Proteins from Gels", *Electrophoresis*, vol. 17, 1996, pp. 839-847.

CAL007—Rabilloud, "Detecting Proteins Separated by 2-D Gel Electrophoresis", *Analytical Chemistry*, vol. 72, Jan. 1, 2000, pp. 48A-55A.

CAL008—Shevchenko et al., "Mass Spectrometric Sequencing of Proteins from Silver-Stained Polyacrylamide Gels", *Analytical Chemistry*, vol. 68, No. 5, Mar. 1, 1996, pp. 850-858.

CAL009—Shevchenko et al., "Linking Genome and Proteome by Mass Spectrometry: Large-Scale Identification of Yeast Proteins from Two Dimensional Gels", *Proc. Natl. Acad. Sci. USA*, vol. 93, Dec. 1996, pp. 14440-14445.

CAL010—Gygi et al., "Evaluation of Two-Dimensional Gel Electrophoresis-Based Proteome Analysis Technology", *Proc. Natl. Acad. Sci. USA*, vol. 97, No. 17, Aug. 15, 2000, pp. 9390-9395.

CAL011—Smith, "Probing Proteomes—Seeing the Whole Picture?", *Nature Biotechnology*, vol. 18, Oct. 2000, pp. 1041-1042.

CAL012—Burgi et al., "Optimization in Sample Stacking for High-Performance Capillary Electrophoresis", *Analytical Chemistry*, vol. 63, No. 18, Sep. 15, 1991, pp. 2042-2047.

CAL013—Chien et al., "On-Column Sample Concentration Using Field Amplification in CZE", *Analytical Chemistry*, vol. 64, No. 8, Apr. 15, 1992, pp. 489A-496A.

CAL014—Chien et al., "Sample Stacking of an Extremely Large Injection Volume in High-Performance Capillary Electrophoresis", *Analytical Chemistry*, vol. 64, No. 9, May 1, 1992, pp. 1046-1050.

CAL015—Burgi et al., "On-Line Sample Preconcentration for Capillary Electrophoresis", in *Handbook of Capillary Electrophoresis*, Edited by James P. Landers, CRC Press, 1997, pp. 479-493.

CAL016—Ramsey et al., "Generating Electrospray from Microchip Devices Using Electroosmotic Pumping", *Analytical Chemistry*, vol. 69, No. 6, Mar. 15, 1997, pp. 1174-1178.

CAL017—Oleschuk et al., "Analytical Microdevices for Mass Spectrometry", *Trends in Analytical Chemistry*, vol. 19, No. 6, 2000, pp. 379-388.

CAL018—Gatlin et al., "Protein Identification at the Low Femtomole Level from Silver-Stained Gels Using a New Fritless Electrospray Interface for Liquid Chromatography—Microspray and Nanospray Mass Spectrometry", *Analytical Biochemistry*, vol. 263, 1998, Article No. AB982809, pp. 93-101.

CAL019—Scheler et al., "Peptide Mass Fingerprint Sequence Coverage from Differently Stained Proteins on Two-Dimensional Electrophoresis Patterns by Matrix Assisted Laser Desorption/Ionization-Mass Spectrometry (MALDI-MS)", *Electrophoresis*, vol. 19, 1998, pp. 918-927.

CAL020—Ramsamooj et al., "Differential Expression of Proteins in Radioresistant and Radiosensitive Human Squamous Carcinoma Cells", *Journal of the National Cancer Institute*, vol. 84, No. 8, Apr. 15, 1992, pp. 622-628.

CAL021—Wilkins et al., "Proteome Research: New Frontiers in Functional Genomics", Published by Springer, Berlin, 1997, pp. 187-219.

CAL022—Ostergaard et al., "Psoriasin (S100A7): A Putative Urinary Marker for the Follow-Up of Patients with Bladder Squamous Cell Carcinomas", *Electrophoresis*, vol. 20, 1999, 349-354.

CAL023—Page et al., "Proteomic Definition of Normal Human Luminal and Myoepithelial Breast Cells Purified from Reduction Mammoplasties", *Proc. Natl. Acad. Sci. USA*, vol. 96, No. 22, Oct. 26, 1999, pp. 12589-12594.

CAL024—Wilm et al., "Femtomole Sequencing of Proteins from Polyacrylamide Gels by Nano-Electrospray Mass Spectrometry", *Nature*, vol. 379, Feb. 1, 1996, pp. 466-469.

CAL025—Lottspeich, "Proteome Analysis: A Pathway to the Functional Analysis of Proteins", *Angew. Chem. Int. Ed.*, vol. 38, 1999, pp. 2476-2492.

CAL026—Pandey et al., "Proteomics to Study Genes and Genomes", Nature, vol. 405, Jun. 15, 2000, pp. 837-846.

CAL027—Binz et al., "A Molecular Scanner to Automate Proteomic Research and to Display Proteome Images", *Analytical Chemistry*, vol. 71, No. 21, Nov. 1, 1999, pp. 4981-4988.

CAL028—Bienvenut et al., "Toward a Clinical Molecular Scanner for Proteome Research: Parallel Protein Chemical Processing Before and During Western Blot", *Analytical Chemistry*, vol. 71, No. 21, Nov. 1, 1999, pp. 4800-4807.

CAL029—Hjerten et al., "Adaptation of the Equipment for High-Performance Electrophoresis to Isoelectric Focusing", *Journal of Chromatography*, vol. 346, 1985, pp. 265-270.

CAL030—Hjerten et al., "Carrier-Free Zone Electrophoresis, Displacement Electrophoresis, and Isoelectric Focusing in a High-Performance Electrophoresis Apparatus", *Journal of Chromatography*, vol. 403, 1987, pp. 47-61.

CAL031—Kilar et al., "Fast and High Resolution Analysis of Human Serum Transferrin by High Performance Isoelectric Focusing in Capillaries", *Electrophoresis*, vol. 10, 1989, pp. 23-29.

CAL032—Yefimov et al., "Transfer of SDS-Proteins from Gel Electrophoretic Zones into Mass Spectrometry, Using Electroelution of the Band into Buffer Without Sectioning of the Gel", *Journal of Biochemical and Biophysical Methods*, vol. 42, 2000, pp. 65-78.

CAL033—Yefimov et al., "Recovery of Sodium Dodecyl Sulfate-Proteins from Gel Electrophoretic Bands in a Single Electroelution Step for Mass Spectrometry Analysis", *Analytical Biochemistry*, vol. 284, 2000, pp. 288-295.

CAL034—Galvani et al., "Letter to the Editor", *Rapid Communications in Mass Spectrometry*, vol. 14, 2000, pp. 721-723.

CAL035—Clarke et al., "One Step Microelectroelution Concentration Method for Efficient Coupling of Sodium Dodecylsulfate Gel Electrophoresis and Matrix-Assisted Laser Desorption Time-of-Flight Mass Spectrometry for Protein Analysis", *Journal of the American Society of Mass Spectrometry*, vol. 9, 1998, pp. 88-91.

CAL036—Tomlinson et al., Improved On-Line Membrane Preconcentration—Capillary Electrophoresis (mPC-Ce), *Journal of High Resolution Chromatography*, vol. 18, Jun. 1995, pp. 381-383.

CAL037—Timperman et al., "Peptide Electroextraction for Direct Coupling of In-Gel Digests with Capillary LC—MS-MS for Protein Identification and Sequencing", *Analytical Chemistry*, vol. 72, No. 17, Sep. 1, 2000, pp. 4115-4121.

CAL038—Guttman et al., "Rapid Analysis of Covalently and Non-Covalently Fluorophore-Labeled Proteins Using Ultra-Thin-Layer Sodium Dodecylsulfate Gel Electrophoresis", *Journal of Chromatography A*, vol. 894, 2000, pp. 329-335.

CAL039—CSAPO et al., "Automated Ultra-Thin-Layer SDS Gel Electrophoresis of Proteins Using Noncovalent Fluorescent Labeling", *Analytical Chemistry*, vol. 72, No. 11, Jun. 1, 2000, pp. 2519-2525.

CAL040—Shoji et al., "Electrophoretic Recovery of Proteins from Polyacrylamide Gel", *Journal of Chromatography A*, vol. 698, 1995, pp. 145-162.

CAL041—CAPLUS abstract for Domingo (ES 2078878 A1).

CAL042—CAPLUS abstract for Grushka et al. ("Effect of Temperature Gradients on the Efficiency of Capillary Zone Electrophoresis Separations", *Analytical Chemistry*, (1989), 61(3); 241-6).

CAL043—CAPULS abstract for Guttman et al. ("Effect of Temperature on the Separation of DNA Restriction Fragments in Capillary Gel Electrophoresis", *Journal of Chromatography*, (1991), 559(1-2); 285-94).

CAL044—CAPLUS abstract for Zhang et al. ("The Effect of Column Temperature on the Migration Teimes of Peptides in Free-Solution Capillary Electrophoresis", *Journal of Liquid Chromatography*, (1993), 16(17); 3689-97).

CAL045—Gao et al., "High-Throughput Detection of Unknown Mutations by Using Multiplexed Capillary Electrophoresis with Poly(vinylpyrrolidone) Solutions", *Analytical Chemistry*, vol. 72, No. 11, Jun. 1, 2000, pp. 2499-2506.

CAL046—Gottschlich et al., "Two-Dimensional Electrochromatography/Capillary Electrophoresis on a Microchip", *Analytical Chemistry*, vol. 73, No. 11, Jun. 1, 2001, pp. 2669-2674.

CAL047—Rocklin et al., "A Microfabricated Fluidic Device for Performing Two-Dimensional Liquid-Phase Separations", *Analytical Chemistry*, vol. 72, No. 21, Nov. 1, 2000, pp. 5244-5249.

CAL048—Becker et al., "Planar Quartz Chips with Submicron Channels for Two-Dimensional Capillary Electrophoresis Applications", *J. Micromech. Microeng.*, vol. 8, 1998, pp. 24-28.

CAL049—Liu et al., "Two-Dimensional Separations: Capillary Electrophoresis Coupled to Channel Gel Electrophoresis", *Analytical Chemistry*, vol. 68, No. 22, Nov. 15, 1996, pp. 3928-3933.

CAL050—Wang et al., "Integrated Capillary Isoelectric Focusing/Nano-reversed Phase Liquid Chromatography Coupled with ESI-MS for Characterization of Intact Yeast Proteins", *Journal of Proteome Research*, vol. 4, No. 1, Jan. 6, 2005, pp. 36-42.

CAL051—Chen et al., "Capillary Isoelectric Focusing-Based Multidimensional Concentration/Separation Platform for Proteome Analysis", *Analytical Chemistry*, vol. 75, No. 13, Jul. 1, 2003, pp. 3145-3152.

CAL052—Chen et al., "Integration of Capillary Isoelectric Focusing with Capillary Reversed-Phase Liquid Chromatography for Two-Dimensional Proteomics Separations", *Electrophoresis*, vol. 23, 2002, pp. 3143-3148.

CAL053—Vissers et al., "Two-Dimensional Capillary Liquid Chromatography Based on Microfractionation", *Journal of Microcolumn Separations*, vol. 11, No. 4, 1999, pp. 277-286.

CAL054—Mechref et al., "Structural Investigations of Glycoconjugates at High Sensitivity", *Chemical Reviews*, vol. 102, 2002, pp. 321-369.

CAL055—Stroink et al., "On-Line Multidimensional Liquid Chromatography and Capillary Electrophoresis Systems for Peptides and Proteins", *Journal of Chromatography B*, vol. 817, 2005, pp. 49-66.

CAL056—Madou, Marc J., "Fundamentals of Microfabrication: The Science of Miniaturization", *CRC Press*, 2002, p. 568, ISBN 0849308267, 4 pages.

\* cited by examiner

TWO-DIMENSIONAL MICROFLUIDICS FOR PROTEIN SEPARATIONS AND GENE ANALYSIS

CROSS-REFERENCE TO RELATED APPLICATIONS

This application is: (1) a continuation-in-part of U.S. patent application Ser. No. 10/135,385, filed May 1, 2002, now U.S. Pat. No. 6,929,730, which claims priority to U.S. Provisional Application No. 60/287,801, filed May 1, 2001, each of which is hereby incorporated herein by reference in their entirety; and (2) a continuation-in-part of U.S. patent application Ser. No. 10/135,386, filed May 1, 2002, now U.S. Pat. No. 6,974,526, which claims priority to U.S. Provisional Application No. 60/287,754, filed May 1, 2001, each of which is hereby incorporated herein by reference in their entirety.

GOVERNMENT LICENSE RIGHTS

The U.S. Government has a paid-up license in this invention and the right in limited circumstances to require the patent owner to license others on reasonable terms as provided for by the terms of Grant Numbers: R43CA092819, and R43GM062738, awarded by the National Institutes of Health, and Grant Number: DAAH01-02-C-R136, awarded by the Defense Advanced Research Projects Agency.

FIELD OF THE INVENTION

The invention relates to a system and method for using a microfluidic apparatus for performing two-dimensional separations of biomolecular materials.

BACKGROUND OF THE INVENTION

Existing protein analysis technology is largely based upon two-dimensional polyacrylamide gel electrophoresis (2-D PAGE), which has undeniably assumed a major role and is central to much of what is now described as "proteomics." Typically, proteins are separated by charge in a first dimension, based on isoelectric focusing in a pH gradient medium, and by size in a second dimension, based on molecular weight in a polyacrylamide gel containing sodium dodecyl sulfate (SDS). When proteins are radiolabeled, or stained, their positions in the gel are detected by autoradiography, or densitometry, respectively.

Despite the selectivity of 2-D PAGE, existing techniques are a collection of manually intensive procedures and time-consuming tasks prone to irreproducibility and poor quantitative accuracy. Thus, automated, high resolution, rapid, reproducible, and ultrasensitive 2-D separation techniques would be advantageous for large-scale analysis of proteins.

Microfluidic platforms offer fast, accurate, and low cost electrokinetic systems for high-throughput 2-D PAGE. One drawback of existing systems is a lack of methodology to detect protein separations in microchannels. Performance of the isoelectric focusing and the size based separation can be monitored by detecting the proteins in microchannels. A robust detection system of proteins in microchannels, is not only important for identification of proteins, but also important for quantification of proteins, with accuracy and resolution.

Another drawback of the application of existing microfluidic techniques to 2-D PAGE devices is a lack of methods to introduce different separation media into different dimensions in the same unit. Performing both charge and size based separations in one miniaturized 2-D PAGE device is desirable for high-throughput purpose.

Another drawback of the application of existing microfluidic techniques to 2-D PAGE devices is a lack of methods to transfer proteins simultaneously from first to second dimensions without significant loss in resolution. In existing methods, protein analytes are continuously sampled in the first dimension and transferred to the second dimension. To date, sufficient resolution has not been achieved using existing methods.

A problem with microfluidic devices for 2-D DNA gel electrophoresis is the lack of convenient, effective methodology to transfer DNA molecules from a first dimension to a second dimension after separation of molecules in the first dimension. Microfluidic devices for 2-D DNA gel electrophoresis also suffer from the lack of a convenient method or device for high throughput and high resolution second dimension separation. Current approaches using DGGE or other currently available gel based methods for this sequence-dependent separation in microfluidic devices have limitations in handling for high throughput purposes.

These and other drawbacks exist.

SUMMARY OF THE INVENTION

One advantage of the invention is that it overcomes these and other drawbacks in existing systems by providing a microfluidic apparatus for performing 2-D biomolecular separations. The microfluidic 2-D device may comprise first and second planar substrates which include at least a first dimension microchannel extending in a first direction and an array of second dimension microchannels extending in a second direction, preferably, orthogonal to the first dimension. The ends of at least some of the microchannels are in fluid communication with a plurality of reservoirs. The substrates may further comprise a number of microchannels and reservoirs. The reservoirs are in electrical communication with a plurality of electrodes and voltage power sources. The device enables two dimensional separations of proteins, DNA, and other biomolecules. According to another aspect of the invention, an isoelectric point based separation is enabled in a first dimension, and a size based separation in a second dimension.

Another advantage of the invention is that it enables introduction of two different media in different microchannels of the same 2-D microfluidic device (e.g., a media for isoelectric point based separation, and a media for size based separation). In one embodiment, a pressure filling technique may be used to introduce the two different media. Electroosmotic or other electrokinetic pumping may also be used to introduce the two different media. In some embodiments, a polymeric membrane sandwiched between the upper and the lower microchannels may serve as a hydrodynamic barrier, enabling the introduction of two different separation media in the upper and the lower microchannels. Other filling approaches may be used.

Another advantage of the invention is that it enables simultaneous transfer of proteins from first dimension microchannels to second dimension microchannels (e.g., by changing the electric potentials at the reservoirs connected to the microchannels). Any separation accomplished in the first dimension may be completely retained upon transfer to the second dimension. In some embodiments, the transfer of material (e.g. proteins) from the first to the second dimension may be achieved by hydrodynamic pressure at the reservoirs connecting first dimension microchannels. In other embodiments, isoelectric focused proteins in the first dimension may be electrokinetically injected into the second dimension, by altering the electric potentials at the reservoirs connecting microchannels. This simultaneous transfer approach also significantly simplifies the procedures compared to those involved in continuous sampling and separation of the eluants from the first dimension.

Another advantage of the invention is that it enables high resolution detection of proteins in microchannels. In one embodiment, proteins may be covalently labeled with a florescent dye. During first and second dimension separations, the labeled proteins may be monitored using a florescent detector attached to the microfluidic system. In some embodiments, microchannels fabricated by polydimethylsiloxane (PDMS) substrates may be used which provide low florescence background during detection and enable better signal to background resolution. According to another embodiment of the invention, laser induced florescent detection (LIFD) may be employed for the detection of SDS-protein complexes using non-covalent, environment-sensitive, fluorescent probes.

In one embodiment, separation in the second dimension may be performed using a temperature gradient (e.g., a spatial or temporal temperature gradient). According to one embodiment of the invention, the biomolecular material comprises DNA and the first dimension separation is a sized-based separation and the second dimension separation is a sequence-based separation.

According to another aspect of the invention, to automate and increase the throughput of 2-D DNA gel electrophoresis, a 2-D plastic microfluidic network is provided for rapidly and accurately resolving DNA fragments based on their differences in size and sequence. The first dimension size-based separation may be performed in a known manner. Instead of continuously sampling DNA analytes eluted from the first size-separation dimension, one aspect of the invention relates to electrokinetically and simultaneously transferring the size-separated DNA fragments from the first dimension (e.g., a microchannel extending from left to right and connecting first and second reservoirs) to a microchannel array between third (and in some embodiments) and fourth reservoirs for performing a sequence-dependent separation. Preferably, the electrokinetic transfer occurs simultaneously in each of the second dimension microchannels. Increased throughput can be achieved by rapid size-based separations (e.g., in the range of 0-200 seconds) followed by simultaneous transfer of size-separated DNA fragments together with parallel sequence-dependent separations in the second dimension. This simultaneous transfer approach also significantly simplifies the procedures compared to those involved in continuous sampling and separation of the eluants from the first dimension.

According to another aspect of the invention, instead of using denaturing reagents such as urea and formamide, DNA fragments (or other materials) in the second dimension are resolved by using a temporal or a spatial temperature gradient. Since the "melting" of DNA fragments is a function of base sequence with GC-rich regions being more stable than AT-rich regions, sequence differences between fragments may be revealed as migration differences. Thus, the invention provides an automated, cost-effective, high throughput, rapid, and reproducible 2-D microfluidic gene scanner. Ultrasensitive measurements of these DNA fragments may then be achieved with an integrated optical detection system (e.g., by using laser-induced fluorescence detection (LIFD) with the addition of intercalating dyes such as ethidium bromide and thiazole orange in the electrophoresis buffer). This 2-D DNA separation platform can perform effectively with even minute DNA samples and enables automation and true system integration of size and sequence-dependent separations with real time fluorescence detection and imaging.

According to one embodiment, the second dimension transfer and the second dimension separation may occur by applying an electric field along the length of the one or more second-dimension microchannels while applying a temperature gradient, thereby denaturing the biomolecules and further separating the biomolecules based on their migration time through the gel contained therein.

According to some embodiments of the invention, various combinations and configurations of microchannels and reservoirs may be implemented to control intersection voltages and enable advantageous separation techniques. For example, in addition to first and second dimension microchannels, other microchannels (e.g., tertiary) may be implemented to enable advantageous separation techniques. Likewise, voltage control microchannels may be implemented to enable advantageous manipulation of samples. In addition, other reservoirs, grouping of microchannels (e.g., parallel groups feeding into respective reservoirs, multiple groups feeding into single, common microchannels, etc.) resistive elements and other configurations may enable advantageous sample separation and manipulation.

According to one embodiment a spatial temperature gradient is formed along the length of the one or more second-dimension microchannels. According to another embodiment, a temporal gradient is used. The temporal or spatial temperature gradient may be created using a variety of techniques including internal and external heat sources.

One aspect of the invention relates to 2-D microfluidic networks formed in plastic substrates (e.g., using template imprinting technologies) and integration of this technology with the computerized design of PCR primers that generate a large number of DGGE-optimized target fragments in one single reaction, i.e. a PCR multiplex. The combination of the high throughput and cost-effective 2-D microfluidic gene scanner with the principle of the PCR multiplex may enable an extensive parallel gene scanner for mutation detection in large human disease genes, for exploring human genetic variability in population-based studies, and for other purposes. This may facilitate genome typing of human individuals, comprehensive mutation analysis, and other advantages.

Another advantage of the invention is that it enables integration of 2-D microfluidic networks formed in plastic substrates (e.g., using template imprinting, injection molding, laser machining, or a combination of these technologies) with LIFD and mass spectrometry detection for automation, high throughput, reproducibility, robustness, and ultrahigh resolution. These capabilities are advantageous for large-scale proteome analysis and for "differential display" of protein expressions under various physiological conditions.

The microfluidic 2-D PAGE of the present invention may be advantageous for the study of organisms having fully sequenced genomes, and may identify proteins (and their modifications in many cases) as well as provide quantitative measurements of expression levels. Other uses will be apparent.

These and other features and advantages of the invention will be more fully appreciated from the detailed description of the preferred embodiments and the drawings attached hereto. It is also to be understood that both the foregoing general description and the following detailed description are exemplary and not restrictive of the scope of the invention.

DETAILED DESCRIPTION

Figure 1:
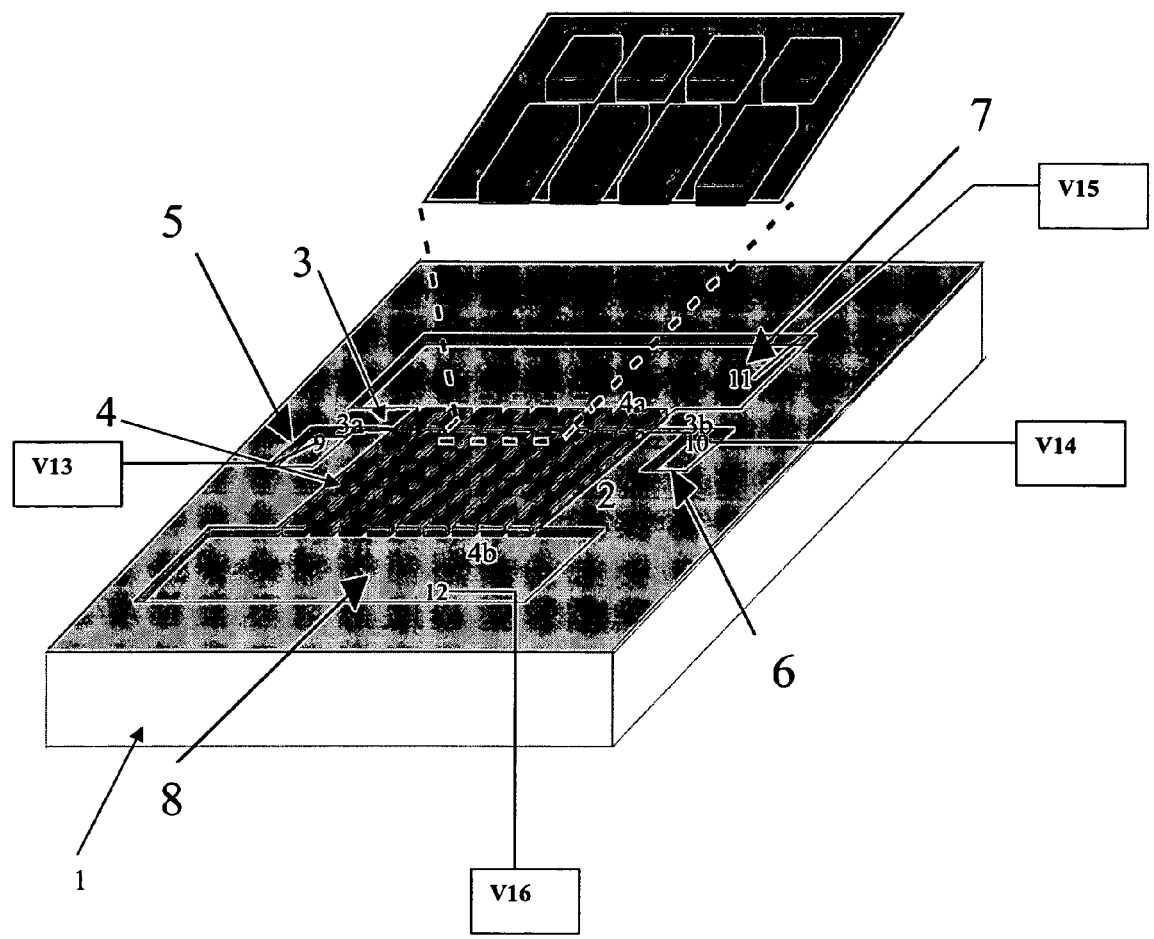
FIG. 1 is a schematic of a microfluidic device with inlet and outlet reservoirs according to one embodiment of the invention.

According to one embodiment of the invention as illustrated in FIG. 1, for example, a microfluidic 2-D gel electrophoresis apparatus is provided. Microfluidic 2-D gel electrophoresis apparatus may comprise a first planar substrate 1 containing one or more first-dimension microchannels 3 for first dimension separation, as well as a second planar substrate 2 (bonded to first planar substrate 1) to provide enclosure for one or more second-dimension microchannels 4 for second dimension separation.

According to one embodiment, the first-dimension microchannel 3 may extend in a first direction, while an array of one or more second-dimension microchannels 4 may extend from, or intersect with, the first-dimension microchannel 3 in a second direction. Preferably the second direction is orthogonal to the first direction. The first-dimension microchannel 3 may have a first end 3a and a second end 3b. Similarly, an array of one or more second-dimension microchannels 4 may each have a first end 4a and a second end 4b.

According to one embodiment the first end 4a of the one or more second-dimension microchannels 4 may intersect the first-dimension microchannel 3 at various locations along the length of the first dimension microchannel.

According to one embodiment, as illustrated in FIG. 1, the apparatus may further comprise one or more reservoirs (5, 6, 7, 8) and voltage sources (V13, V14, V15, V16) associated with each of the reservoirs, respectively. For example, a first reservoir 5 may be in fluid communication with a first end 3a of the first microchannel 3, and a second reservoir 6 may be in fluid communication with a second end 3b of the first microchannel 3. Additionally, a third reservoir 7 may be in fluid communication with a first end 4a of each of the second dimension microchannels 4, and a fourth reservoir 8 may be in fluid communication with a second end 4b of the second dimension microchannels 4. In other embodiments, some of which are described herein, different configurations of microchannels and reservoirs may be used. Not all embodiments may use 4 reservoirs. More or less may be used.

According to one embodiment of the invention, the one or more reservoirs (5-8) may be formed in the first 1 or second 2 substrate, and a plurality of separation electrodes (9, 10, 11, 12) may be provided. A first end (indicated schematically) of the separation electrodes (9-12) may be located in electrical communication with the reservoirs 5-8, respectively. A second end (indicated schematically) of the separation electrodes 9-12 may be attached to one or more high voltage power supplies (V13, V14, V15, V16). One or more of electrodes 9-12 may also be connected to ground potential (e.g., ~0 Volts) (not shown in the figure).

Figure 2A:
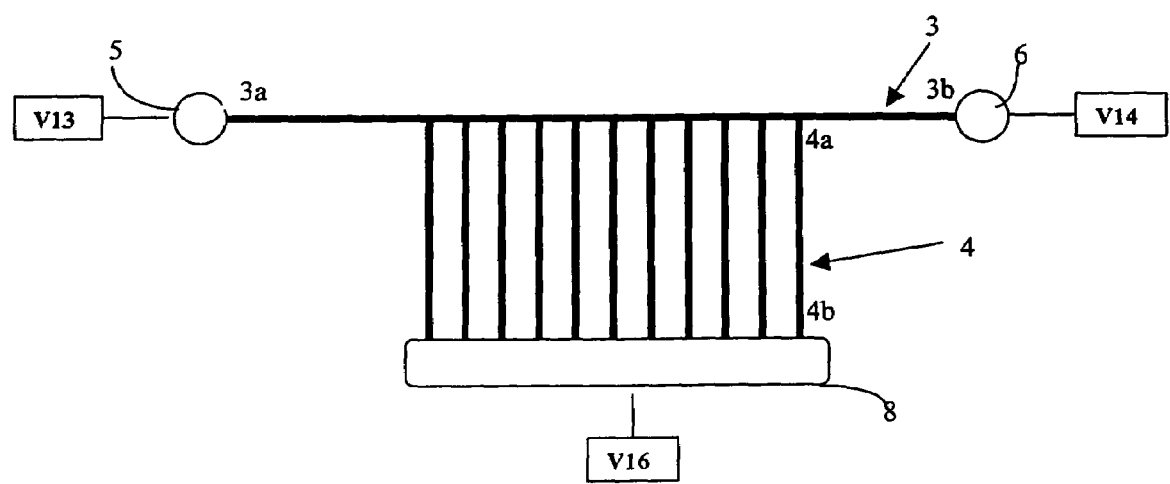
FIG. 2A is a schematic of a microfluidic device lacking second dimensional inlet reservoir according to one embodiment of the invention.

As illustrated in FIG. 1, the device has one or more inlet 5 and outlet 6 reservoirs at the ends of the first microchannel 3, and one or more inlet 7 and outlet reservoirs 8 at the ends of the second dimension microchannels 4. Other configurations may be used. For example, in one embodiment (as illustrated in FIG. 2A), the first ends 4a of the one or more second dimension microchannels 4 may terminate at one or more points between the first and second ends (3a, 3b) of the first dimension microchannel 3. In this embodiment, no second dimension inlet reservoir is used.

Figure 3:
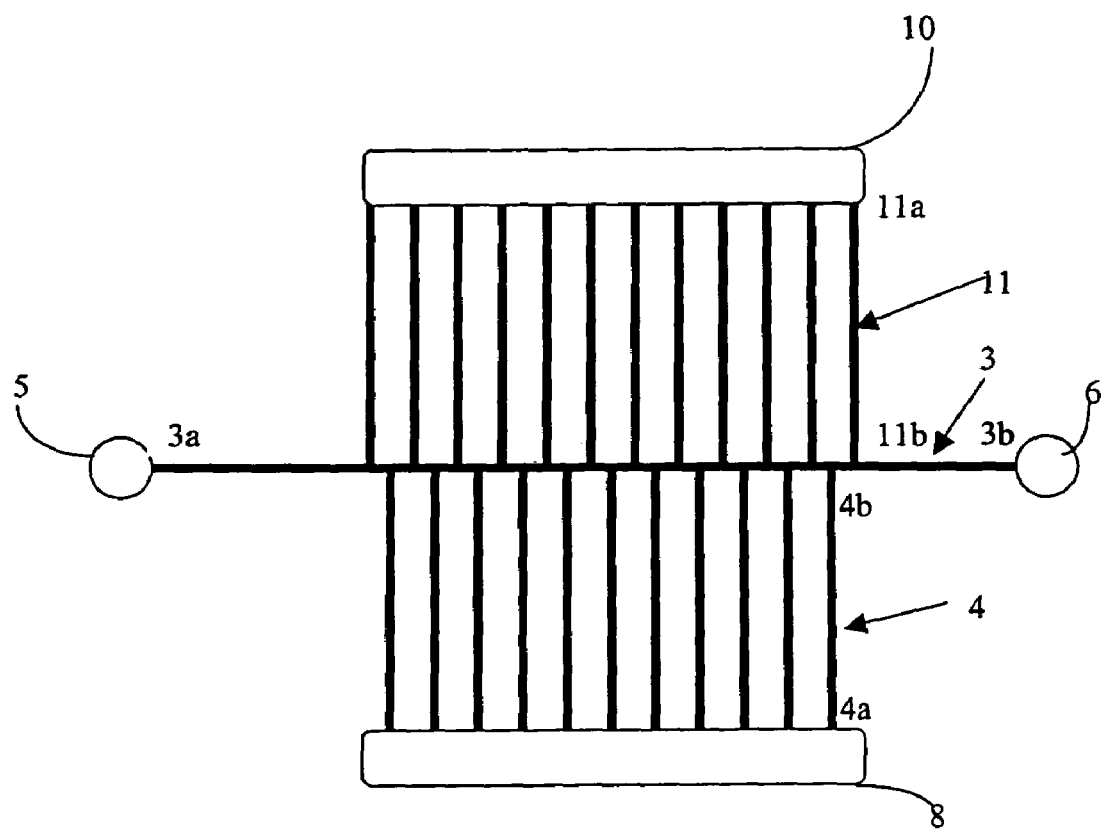
FIG. 3 is a schematic of a microfluidic with tertiary channels for electrokinetic transfer according to one embodiment of the invention.

In another embodiment, as illustrated in FIG. 3, one or more second-dimension separation outlet reservoirs 8 may intersect the first end 4a of the one or more second-dimension microchannels 4, and one or more tertiary inlet reservoirs 10 may intersect the first end 11a of the one or more tertiary microchannels 11. The second end 11b of the one or more tertiary microchannels 11 may terminate at one or more points between the first and second ends (3a, 3b) of the first dimension microchannel 3, and the second ends 4b of the one or more second dimension microchannels 4 may terminate at one or more points between the first and second ends (3a, 3b) of the first dimension microchannel 3. In this embodiment, the one or more points at which the second ends (11b, 4b) of the tertiary microchannels 11 and second dimension microchannels 4 terminate at the first dimension microchannel 3 may be staggered. Preferably, the number of tertiary microchannels 11 is equal to one more than the number of secondary microchannels 4, and the one or more points at which the second ends 4b of the second dimension microchannels 4 terminate at the first dimension microchannel 3 are staggered from the one or more points at which the second ends 11b of the tertiary microchannels 11 terminate at the first dimension microchannel 3 by half the distance between adjacent tertiary microchannels 11. In this embodiment, the one or more second dimension separation inlet reservoirs 7 may be omitted.

In some embodiments, microchannels (e.g. 3, 4) may have depth to width ratio of approximately 1:3. Other ratios and dimensions may be used. For example, microchannels with an average depth of 10 μm may have an average width of 30 μm. However, both depth and width preferably range from 5 to 200 μm. For illustrative purpose, the width mentioned herein is from trapezoidal shaped microchannel cross-sections. Other shapes for microchannel cross-sections may be used, for example rectangular, circular, or semi-circular cross-sections. The microchannels (e.g. 3, 4) can be any suitable length. A preferred length ranges from about 1 to about 10 cm. Other lengths may be used. Some embodiments may have other microchannel dimensions for various applications.

In some embodiments, a plastic substrate such as poly (methylmethacrylate) (PMMA) or polycarbonate may be used for fabrication of the microfluidic 2-D apparatus. In one embodiment, a polydimethylsiloxane (PDMS) layer combined with a rigid substrate is used for fabrication of the 2-D microfluidic apparatus. Non-plastic materials such as glass or silica may also be used to fabricate the 2-D microfluidic apparatus of the present invention.

Spacing between the intersections determines the size of the sample plug being introduced into the second dimension microchannel array 4. The extent of resolution loss during the transfer step is mainly dependent upon the spacing and focused protein bandwidth achieved from isoelectric focusing in the first dimension microchannel 3.

According to one embodiment, microchannels (e.g. 3, 4) may be filled with any suitable carrier ampholyte solution for first dimension separation and any gel solution preferably with SDS for second dimension separation of proteins. A preferred voltage for separation of proteins range from 100 V/cm to 1000 V/cm. A high voltage power supply may be attached to a second end of a selected number of the one or more separation electrodes (e.g., electrodes 9-12). Due to the extremely large surface area to volume ratio of microchannels (e.g. 3, 4) for efficient heat dissipation, the application of high electric voltage enables rapid and excellent separation of proteins in the microfluidic network. In some embodiments, microfluidic device of the present invention is used for separating DNA, peptides, and other biological or chemical composites.

According to one aspect of the invention, the 2-D plastic microfluidic device separates protein analytes with ultrahigh resolution based on their differences in isoelectric point and size. As illustrated in FIG. 1., one or more microchannels 3 extending from left to right in the figure and connecting one or more reservoirs 5 and 6 may be employed for performing a non-native isoelectric focusing separation in a first dimension. Once the first dimension separation is complete, the material (e.g. proteins) may be transferred into a microchannel array connecting one or more reservoirs 8 for performing a parallel and high throughput size-dependent separation. The transfer to the second dimension may occur virtually simultaneously in each microchannel of the second dimension array of microchannels 4. In some embodiments, one or more reservoirs 10 (as illustrated in FIG. 3) at the end of one or more tertiary microchannels 11 may be used for introducing buffer-dye complex during electrokinetic transfer of proteins from first dimension to second dimension.

To monitor the performance of isoelectric focusing in first dimension microchannels 3, proteins may be covalently labeled with a suitable florescent dye and detected by a suitable florescence detector. An example of a fluorescent dye is 5-carboxy fluorescein succinimidyl ester which may be used to label the proteins. Other dyes or labeling techniques may be used. An example of a detector is a Zeiss fluorescence microscope. Other detectors and detection techniques may be used. Because of the large number of amino groups on protein molecules, very small amounts of fluorescein dye is needed. These labeled proteins may be denatured and reduced at approximate concentration of 1 mg/ml for each protein. The proteins may be prepared in a suitable solution (e.g. a solution including urea, dithiothreitol, and Tris-HCl with approximate concentrations of 8M, 100 mM and 0.1 M respectively) with a pH preferably ranging from 4 to 10. The protein solution may be kept under a nitrogen atmosphere for about four hours in room temperature. The denatured and reduced proteins may be desalted using a column preferably by PD-10 column. Eluted proteins may be dried preferably by vacuum and stored at a preferred temperature of about −20° C. These proteins may be reconstituted in the solution containing carrier ampholytes (approximately 2% pharmalyte 3-10) and urea (between 1 and 3 M) for performing non-native isoelectric focusing. Plastic microchannels made out of PDMS substrate are advantageous for isoelectric focusing because they are optically transparent at the wavelengths required for the fluorescence detection of proteins and they provide low fluorescence background. Other materials may be used.

According to one aspect of the invention, two different media are introduced in a 2-D microfluidic network for performing two dimensional separations of proteins. Isoelectric focusing in the first dimension involves the use of carrier ampholytes for the creation of pH gradient in the microchannel. However, size-dependent separation of SDS-protein complexes in the second dimension is based on their differences in electrophoretic mobility inside a polymer sieving matrix.

In one embodiment, a pressure filling approach may be used for introducing two different media into the at least one first dimension microchannel and array of second dimension microchannels respectively. Gel solutions may be introduced into microchannel arrays (e.g., 3, 4) by applying pressure in reservoirs. As illustrated in FIG. 2A, reservoir 8 and the connecting microchannel array 4 may be filled with a polymer gel solution. Various polymers, including polyacrylamide, polyethylene oxide, and branched dextran, can be employed for preparing the gel solution. The gel solution may be introduced into the array by applying pressure at reservoir 8. The flow velocity may be controlled by the pressure gradient, the viscosity of the solution, and the channel dimensions. The filling process may be monitored by adding a preferred fluorescent dye, ethidium bromide (excitation: 514 nm; emission: 604 nm), into the gel solution and using a preferred fluorescent detector, Zeiss fluorescence microscope, equipped with a computer controlled moving stage. The filling may be stopped as soon as the gel solution reaches the intersections of the microchannel array and the channel connecting reservoirs 5 and 6. The solution containing carrier ampholytes for isoelectric focusing separation may then be introduced via pressure from reservoir 5 for filling the channel connecting reservoirs 5 and 6. Because of the low viscosity in the ampholyte solution, the pressure needed for introducing the ampholyte solution is much lower than that required for pushing a polymer gel solution. Thus, a 2-D plastic microfluidic network may be filled with two different separation media using this two-step pressure filling approach. It should be noted that any suitable fluorescent dye may be added to gel and any suitable detector may be used to monitor the filling process.

In another embodiment, the entire plastic microfluidic network may initially be filled with a polymer gel solution by pressure. The pressure level required for filling the microfluidic network depends upon the cross-sectional dimensions and lengths of the microchannels, in addition to the viscosity of the gel solution. In the case of embodiments where the bonding strength between the top and bottom layers of the device is not sufficient to hold the device together during high-pressure filling, an external force may be applied to hold the layers together during the filling process. The filling of the microfluidic network is followed by removal of the polymer gel in the microchannels connecting reservoirs 5 and 6 as illustrated in FIG. 2A. Removal of gel in the first-dimension microchannel may be achieved by applying a pressure to reservoir 5 while leaving reservoir 6 open, and closing all other reservoirs in the device to prevent loss of gel from the second-dimension microchannels. In another embodiment, removal of the gel is achieved using an electroosmotic process. The electroosmotic removal process may be induced by applying a positive electric voltage ranging from 1 to 10 kV at reservoirs 5 containing a preferred salt, NaOH, solution. The speed and completeness of electroosmotic removal approach may be monitored by adding preferred dye ethidium bromide into the gel solution and using a preferred fluorescence detector Zeiss fluorescence microscope equipped with a computer controlled moving stage. The removal speed is expected to increase as the section of microchannel containing NaOH instead of polymer gel solution increases. As soon as the removal process is complete, the solution containing any carrier ampholytes for the isoelectric focusing may then be introduced via pressure from reservoir 5 for filling the first dimension channel connecting reservoirs 5 and 6.

Figure 10:
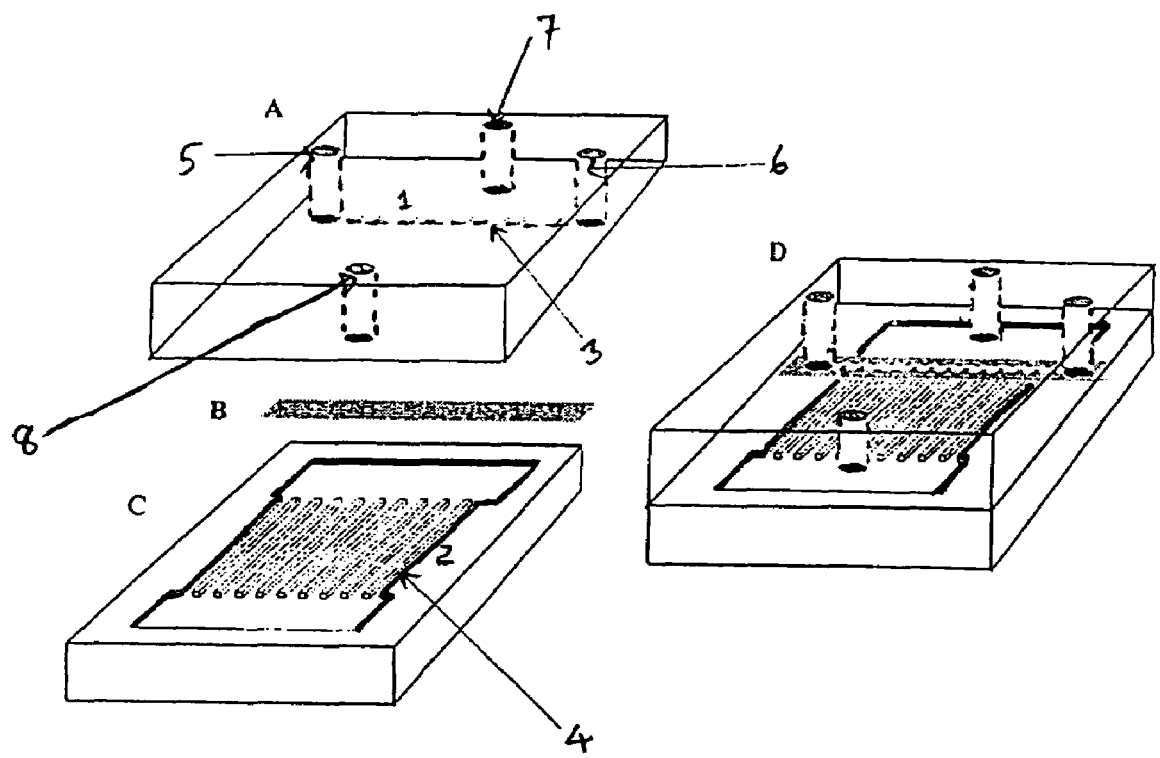
FIG. 10 is a schematic of a microfluidic apparatus with a polymeric membrane strip for introduction of two different media according to one embodiment of the invention.

In yet another embodiment, a preferred polymeric membrane, polyvinylidene fluoride (PVDF), sandwiched between the upper and lower microchannels may serve as a hydrodynamic barrier, providing the initial filling of two different separation media in the upper and lower microchannels. As illustrated in FIG. 10, 2-D protein separation platform may comprise the upper substrate (A) containing two or more reservoirs (5 and 6) for isoelectric focusing in the upper channel 3 and two or more reservoirs (7 and 8) for size based separation in the lower channel array 4, one or more microchannels 3 for performing isoelectric focusing separation, a polymeric membrane strip (B), and the lower substrate containing a microchannel array 4 for performing size-based separation (C). In FIG. 10, D illustrates the assembly of 2-D protein separation platform. According to one aspect of the present invention, the pressure needed for pushing a solution through the membrane with a pore diameter of approximately 0.1 μm may be at least 50 times higher than that required for introducing an aqueous solution into the microchannels. Furthermore, the solutions may take a lower flow-resistance path. Thus, two different electrophoresis media may be separately filled in the upper and lower microchannels. According to another aspect of the present invention, the membrane (B) at the intersections between the upper and the lower microchannels may also serve as injection ports when pressure applied at both ends of the upper microchannel for transferring proteins from the first to the second dimension. In analogy to a dead-end microfiltration process, the focused protein zones in the upper channel may simultaneously permeate through the exposed membrane areas at the nearby intersections.

The methods of the present invention for introducing two different media in the same microfluidic device may also be used for other media in two dimensions for separating DNA, peptides, and other chemical and biological composites.

Figure 2B:
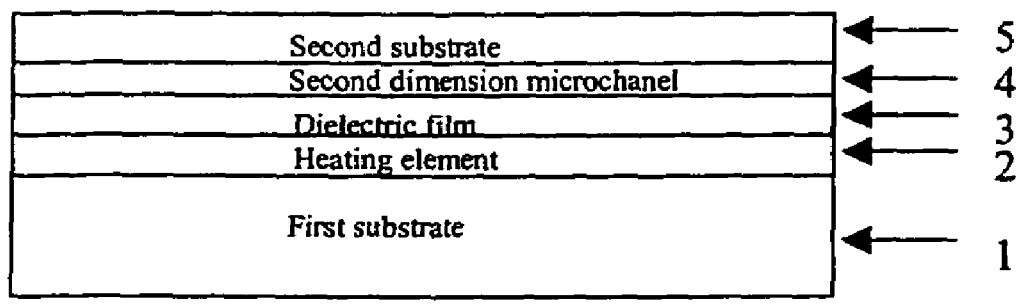
FIG. 2B is a side view of a microfluidic apparatus according to one embodiment of the invention.
Figure 2C:
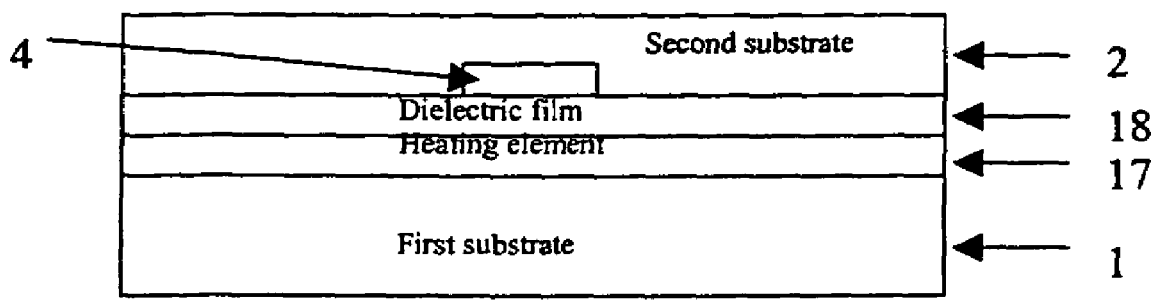
FIG. 2C is a front sectional view of a microfluidic apparatus according to one embodiment of the invention.

According to one embodiment of the invention illustrated in FIGS. 2B and 2C, one or more heating elements 17 may be affixed to an exposed outer surface of the first 1 or second 2 planar substrate for controlling the temperature of the substrates. According to another embodiment of the invention, as illustrated in FIGS. 2B, 2C, one or more heating elements 2 may be bonded between (or otherwise integrated with) the first 1 and second 2 planar substrates. A nonconducting dielectric film 18 may also be placed between the heating elements 17 and the second planar substrate 2 containing one or more microchannels. The one or more heating elements 17 may be shaped to provide a desired temperature distribution across the planar substrate (1, 2) when current is passed through the one or more heating elements 17. In some embodiments, the temperature gradient may comprise a temporal temperature gradient, wherein the one or more heating elements 17 may induce a constant spatial temperature across the entire length and width of the one or more second-dimension microchannels 4, and wherein the constant spatial temperature is varied with time. In other embodiments, a linear spatial temperature profile may be imposed along the length of the one or more second-dimension microchannels 4.

Resistive heating of the one or more heating elements 17 may be used to produce the desired temperature gradient. The heating elements may be made from any suitable material. Platinum may, for example, be used as a preferred heating element 17 material for imposing temperature gradient along microchannels. By using platinum heating elements 17, the local temperature may be monitored by measuring changes in resistance. Platinum may be replaced with other less expensive electrode materials with acceptable temperature coefficients of resistance including, for example, thin film gold, metal foil, conductive polymer(s), conductive ink, electrically-conductive wire, or other materials. Other temperature control structures and techniques may be used.

The spatial temperature gradient may vary from about 20-25° C. at the intersection between the first dimension microchannel 3 and the one or more second-dimension microchannel 4, to about 70-90° C. at the second end 4b of the one or more second-dimension microchannels 4. The spatial temperature gradient may be replaced by a temporal temperature gradient where the one or more heating elements 17 induces a constant spatial temperature across the entire length and width of the one or more second-dimension microchannel 4 and the constant spatial temperature is varied with time. The constant spatial temperature may be varied from an initial temperature of about 20-25° C. to a final temperature of about 70-90° C.

In some embodiments, microchannels (e.g. 3, 4) may have depth to width ratio of approximately 1:3. Other ratios and dimensions may be used. For example, microchannels with an average depth of 10 μm may have an average width of 30 μm. However, both depth and width preferably range from 5 to 200 m. For illustrative purpose, the width mentioned herein is from trapezoidal shaped microchannel cross-sections. Other shapes for microchannel cross-sections may be used, for example rectangular, circular, or semi-circular cross-sections. The microchannels (e.g. 3, 4) can be any suitable length. A preferred length ranges from about 1 to about 10 cm. Other lengths may be used. Some embodiments may have other microchannel dimensions for various applications.

The number of microchannels (e.g. 3, 4, 11) and the spacing therebetween, may be application dependent. The spacing between the second dimension microchannels 4 in the array may determine the size of the sample plug being introduced from the first to the second dimensions. The extent of resolution loss during the transfer step is in part dependent upon the spacing and the DNA bandwidth achieved from size-based separation in the first dimension. Minimal resolution loss may be achieved as there may be no mixing during the electrokinetic transfer of DNA fragments. The number second dimension of microchannels in the array may also range from 10 to 1000, or more.

Separation efficiency and resolution of DNA fragments may be dependent only upon the size-sieving polymer characteristics and the applied electric potential. According to one aspect of the invention, a preferred separation media for electrophoresis in microchannels (e.g. 3, 4) is 1× TBE buffer (89 mM Tris, 89 mM boric acid, 2 mM EDTA) containing 2% poly(ethylene oxide) (PEO). It should be noted that microchannels (e.g. 3, 4) may be filled with any other polymeric media for separating DNA, protein, other biomolecules and chemical composites.

According to one embodiment of the invention, a voltage source (V13, V14, V15, V16) may be attached to a second end (indicated schematically) of a selected number of the one or more separation electrodes (indicated schematically). Due to the extremely large surface area to volume ratio of microchannels for efficient heat dissipation, the application of an electric field may enable rapid and excellent separation of DNA fragments in a microfluidic network. A preferred electric field for separating DNA fragments in the present invention range from 100-1000 V/cm, however, other electric field strengths may be used.

Figure 2D:
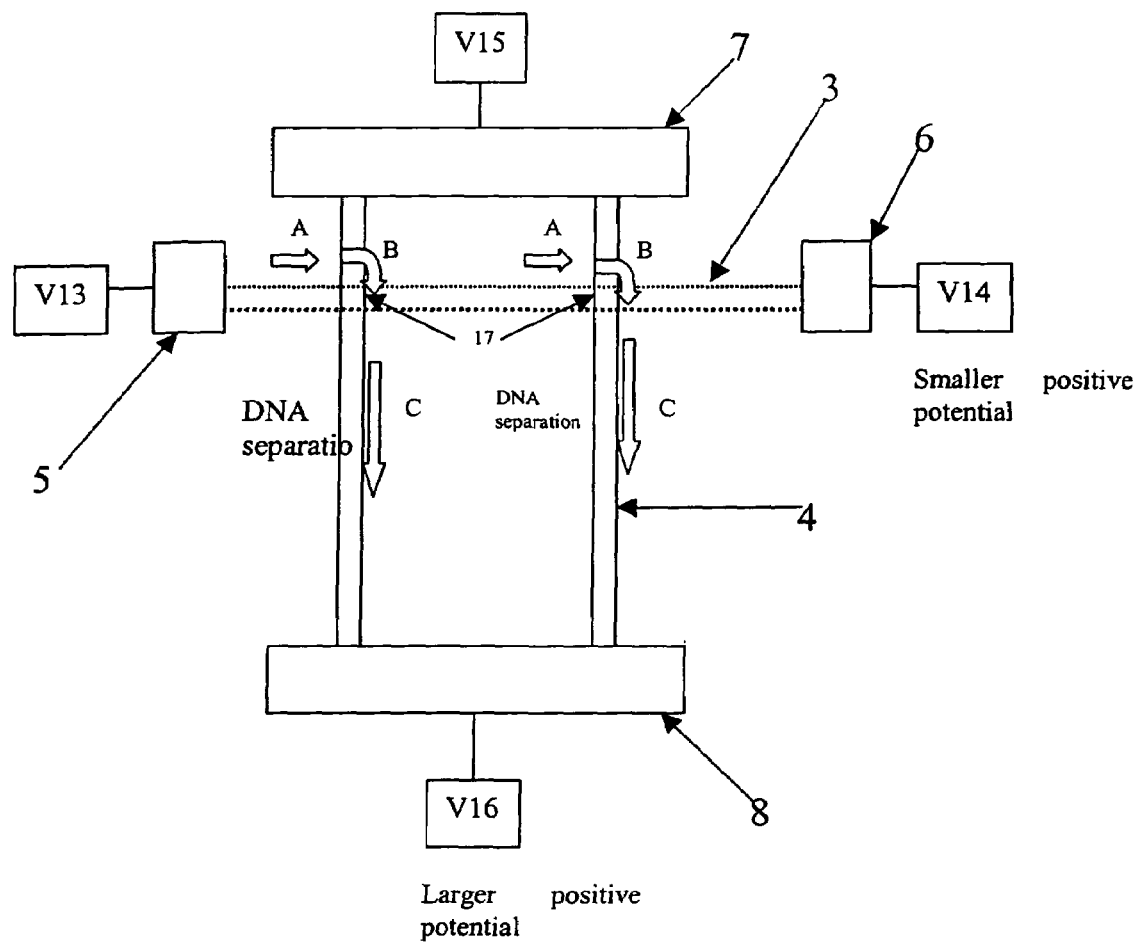
FIG. 2D illustrates electrokinetic transfer of DNA from first dimension to second dimension according to one embodiment of the invention.

According to one embodiment of the invention, as illustrated in FIG. 2D, a relatively low voltage may be applied to the first-dimension outlet reservoir 6, while a grounding voltage may be applied to the first-dimension inlet reservoir 5. The one or more second-dimension inlet reservoirs 7 may be disconnected from any voltage source. Pursuant to this arrangement, when a relatively high electric field is applied along the length of the one or more second-dimension separation microchannels 4, a small electric field may be simultaneously generated along the length of the first-dimension microchannel 3, thereby causing biomolecules to be drawn slightly towards the first-dimension outlet reservoir to ensure efficient transfer of the biomolecules from the first-dimension microchannel into the one or more second dimension microchannels 4.

According one aspect of the present invention, focused proteins in the first dimension are simultaneously transferred to the second dimension by hydrodynamic pressure. To fulfill the requirements of a comprehensive 2-D separation system, the two dimensions should be orthogonal, and any separation accomplished by the first dimension should ideally be retained upon transfer to the second dimension. First dimensional microchannels 3 connecting reservoirs 5 and 6 (as illustrated in FIG. 2A) may be disconnected from the high voltage power supply as soon as the focusing is complete in the first dimension. Equal pressure may then be applied at reservoirs 5 and 6 to drive the solution containing focused protein analytes into the parallel microchannel array. Since the flow resistance in the gel filled microchannel array is extremely high, a constant hydrostatic pressure may be therefore in place across the entire isoelectric focusing channel during this step. Thus, the transfer process may be similar to dead-end membrane filtration. In some embodiments, a highly viscous polymer gel solution at the intersections between the first and second separation dimensions may serve as the individual injection ports for quantitative transfer of focused protein bands. In other embodiments, a polymeric membrane serves as the injection ports for transfer of proteins.

In another aspect of the present invention, focused proteins in the first dimension (e.g. 3) may be electrokinetically transferred to the second dimension (e.g. 4) using end reservoirs (e.g. 5, 6, 8). As soon as the focusing is complete in the first separation dimension, the voltage may be turned off and the solution containing catholyte in reservoir 6 (as illustrated FIG. 2A) may be replaced with a Tris buffer containing SDS and a florescent dye, preferably, SYPRO orange. A positive electric potential may then be reapplied briefly at reservoir 5 for rapid electrokinetic injection and filling of SDS and dye within the first separation dimension (e.g. 3), followed by the incubation of focused proteins with SDS and dye for approximately 5-10 minutes. Since the focused proteins from the first separation dimension (e.g. 3) (non-native isoelectric focusing) may be already denatured and reduced, the rapid formation of SDS-protein complexes may not only prepare protein analytes for size based separation in the second dimension (e.g. 4), but may also establish the foundation for performing electrokinetic protein transfer. The SDS-protein complexes may be electrokinetically injected by grounding reservoir 5 while applying two separate positive potentials at reservoir 6 and 8 using two high voltage power supplies (V14, V16). The smaller positive potential at reservoir 6 may be employed to continuously drive the proteins in the first dimension toward the channel junctions. As soon as the proteins reach the channel junctions, the larger positive potential at reservoir 8 may commence the electrokinetic injection of focused proteins into the second separation dimension.

In yet another aspect of the present invention, focused proteins in the first dimension may be electrokinetically transferred to the second dimension using tertiary reservoirs 10 as illustrated in FIG. 3. This method may involve the use of a set of tertiary microchannels 11 to introduce SDS and a florescent dye, preferably, SYPRO orange. In this method, as soon as the focusing is complete in the first separation dimension (e.g. 3), the voltage may be turned off and the solution in the one or more reservoirs labeled 10 (As illustrated in FIG. 3) may be replaced with a Tris buffer containing SDS and dye. With the potentials at reservoirs 5 and 6 floating, a positive electric potential may then be applied briefly at reservoir 8 for rapid electrokinetic injection and filling of SDS and dye from the tertiary microchannels 11 leading from reservoir 10, through the portion of the first-dimension separation channels 3 between the tertiary microchannels 11, and partially into the second dimension separation channels 4. Once this portion of the microchannel network may be filled, the proteins focused in the first dimension may be incubated with newly introduced SDS and dye for approximately 5-10 minutes. Since the focused proteins from the first separation dimension (non-native isoelectric focusing) may be already denatured and reduced, the rapid formation of SDS-protein complexes may not only prepare protein analytes for the size-based separation in second dimension, but may also establish the foundation for performing electrokinetic protein transfer. After incubation, the SDS-protein complexes may be electrokinetically injected by grounding reservoir 10 while applying a positive potential at reservoir 8 and letting reservoirs 5 and 6 float. Because each tertiary microchannel 11 may intersect the first-dimension microchannel in between two adjacent second-dimension microchannels 4, the applied field may force the majority of SDS-protein complexes that lie within the first dimension microchannel 3 between the extent of the second-dimension microchannels 4 to be transferred into the second dimension (e.g. 4) electrokinetically.

In some embodiments, electrokinetic transfer method may be performed to transfer DNA, peptides, and other chemical or biological composites from one dimension to another dimension of the gel electrophoresis system. As used herein, "electrokinetic transfer method" includes a method or a system which transfer materials from a channel and/or chamber containing structure in one dimension to similar structures in other dimensions, through the application of electric fields to the materials, thereby causing the transfer of the materials.

According to one embodiment of the invention, as illustrated in FIG. 3, a grounding voltage may be applied to the one or more tertiary reservoirs 10, while a high voltage may be applied to the one or more second-dimension outlet reservoirs 8. All other reservoirs may be disconnected from any voltage source. Pursuant to this arrangement, a high electric field is applied along the length of the one or more second-dimension separation microchannels 4, with said electric field passing from the one or more tertiary microchannels 11 through the one or more regions of the first-dimension microchannel 3 between adjacent tertiary 11 and second-dimension microchannels 4, and into the one or more second-dimension microchannels 4, thereby causing biomolecules within the first-dimension microchannel 3 to be drawn into the one or more second-dimension microchannels 4 to ensure efficient transfer of the biomolecules from the first-dimension microchannel 3 into the one or more second dimension microchannels 4.

According to another aspect of the invention, one or more intersection control voltages may be applied to the one or more second-dimension separation inlet reservoirs 7 (as illustrated in FIG. 1) or tertiary inlet reservoirs 10 (as illustrated in FIG. 3), and the one or more second-dimension separation outlet reservoirs 8. This may control the electric field lines at the intersection of the one or more first-dimension separation microchannels 3 and the one or more second-dimension separation microchannels 4 in such a manner that the distribution of biomolecules undergoing separation during the first-dimension separation step are not substantially affected by the intersections.

Figure 4:
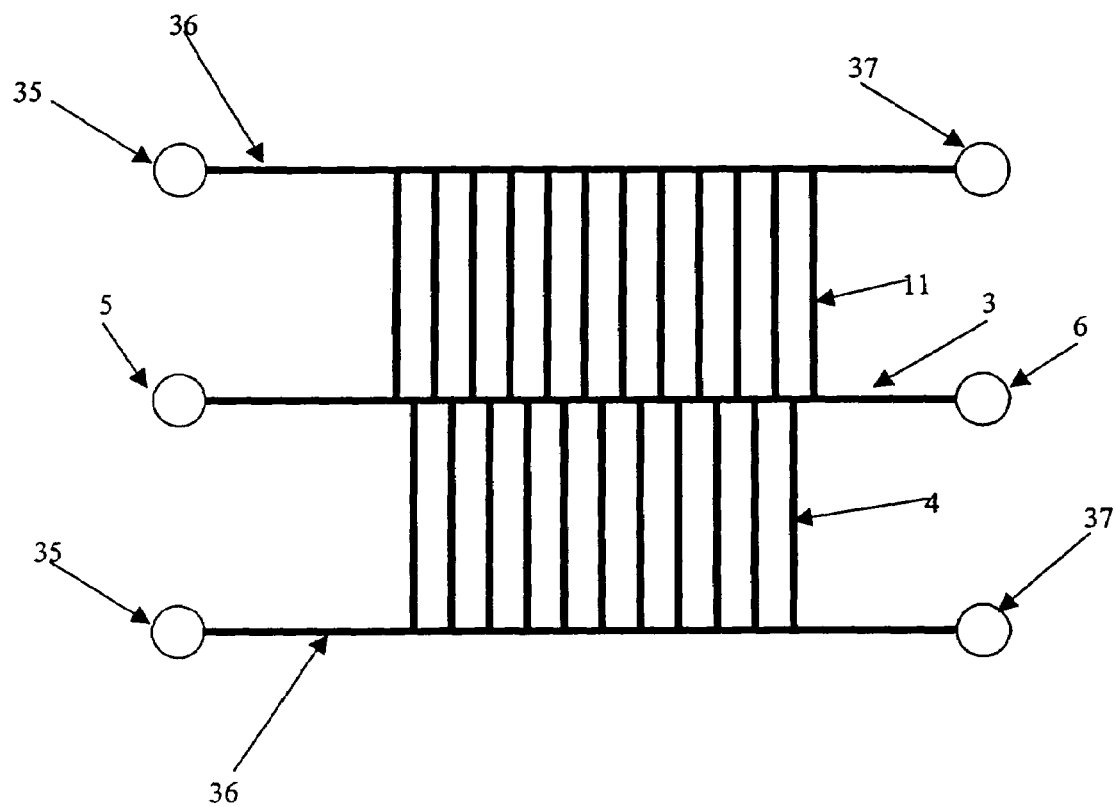
FIG. 4 is a schematic of a microfluidic apparatus with voltage control microchannels according to one embodiment of the invention.

According to an embodiment, as depicted in FIG. 4, the one or more intersection control voltages may be applied using a plurality of voltage sources, wherein one voltage source (not shown in the figure) may be applied to the one or more inlet reservoirs 35 of the one or more voltage control microchannels 36, and a second voltage source may be connected to the one or more outlet reservoirs 37 of the one or more voltage control microchannels 36 to generate a potential gradient along fluid within the one or more voltage control microchannels 36. The geometry of the one or more voltage control microchannels 36 may be selected such that the intersection control voltage at the one or more intersections of the voltage control microchannels 36 and the second-dimension microchannels 4 and/or tertiary microchannels 11 is set by the voltages applied at the voltage control reservoirs (not shown in the figure). Further, the one or more intersection control voltages may be chosen such that the voltage within the one or more second-dimension microchannels 4 and/or tertiary microchannels 11 near the intersection of the one or more first-dimension separation microchannels 3 and the one or more second-dimension separation microchannels 4 (connected to the reservoir at which the intersection control voltage is applied) is slightly different than the voltage within the intersection itself. In this embodiment, the one or more tertiary inlet reservoirs 10 are omitted.

Figure 5:
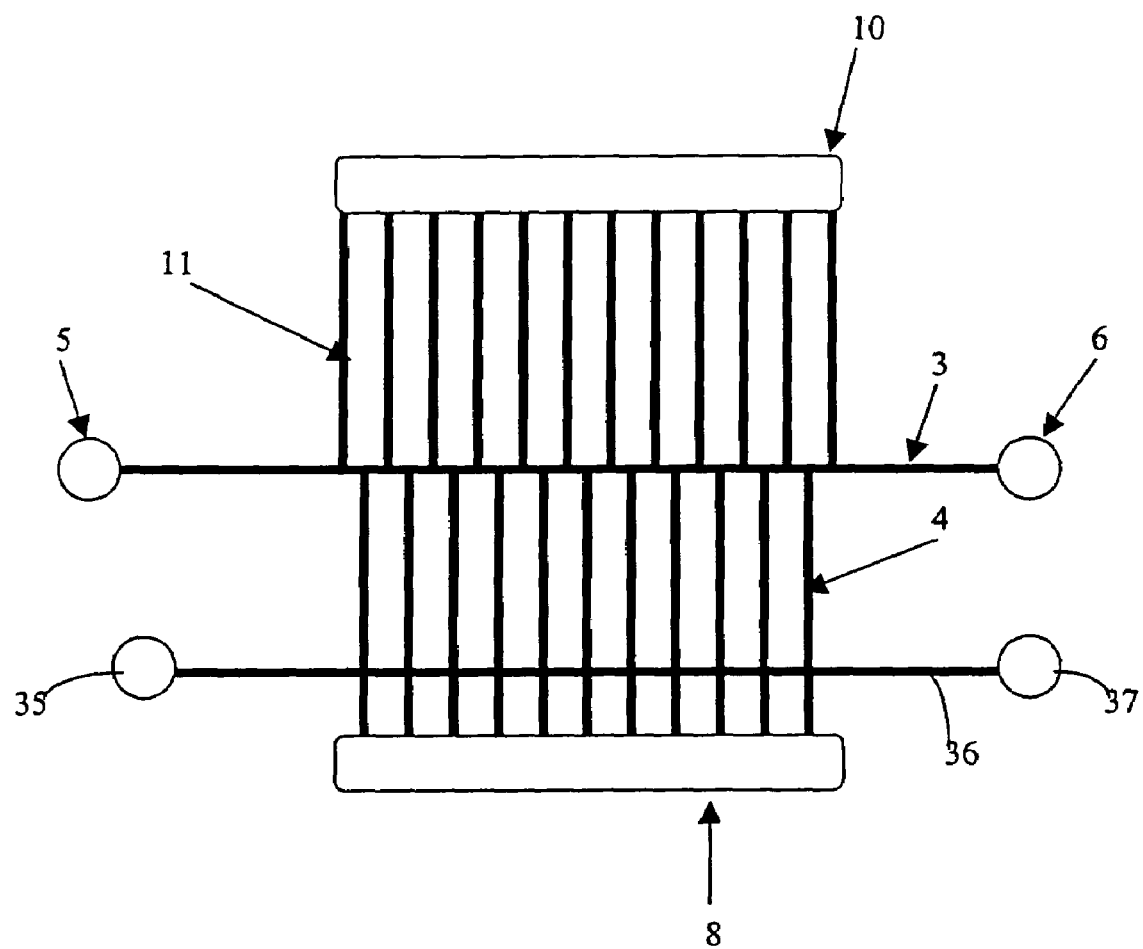
FIG. 5 is a schematic of a microfluidic apparatus comprising voltage control microchannel combined with second-dimension outlet reservoir according to one embodiment of the invention.

According to another aspect of the invention, depicted in FIG. 5, a single voltage control microchannel 36 may be combined with a second-dimension outlet reservoir 8.

Figure 6:
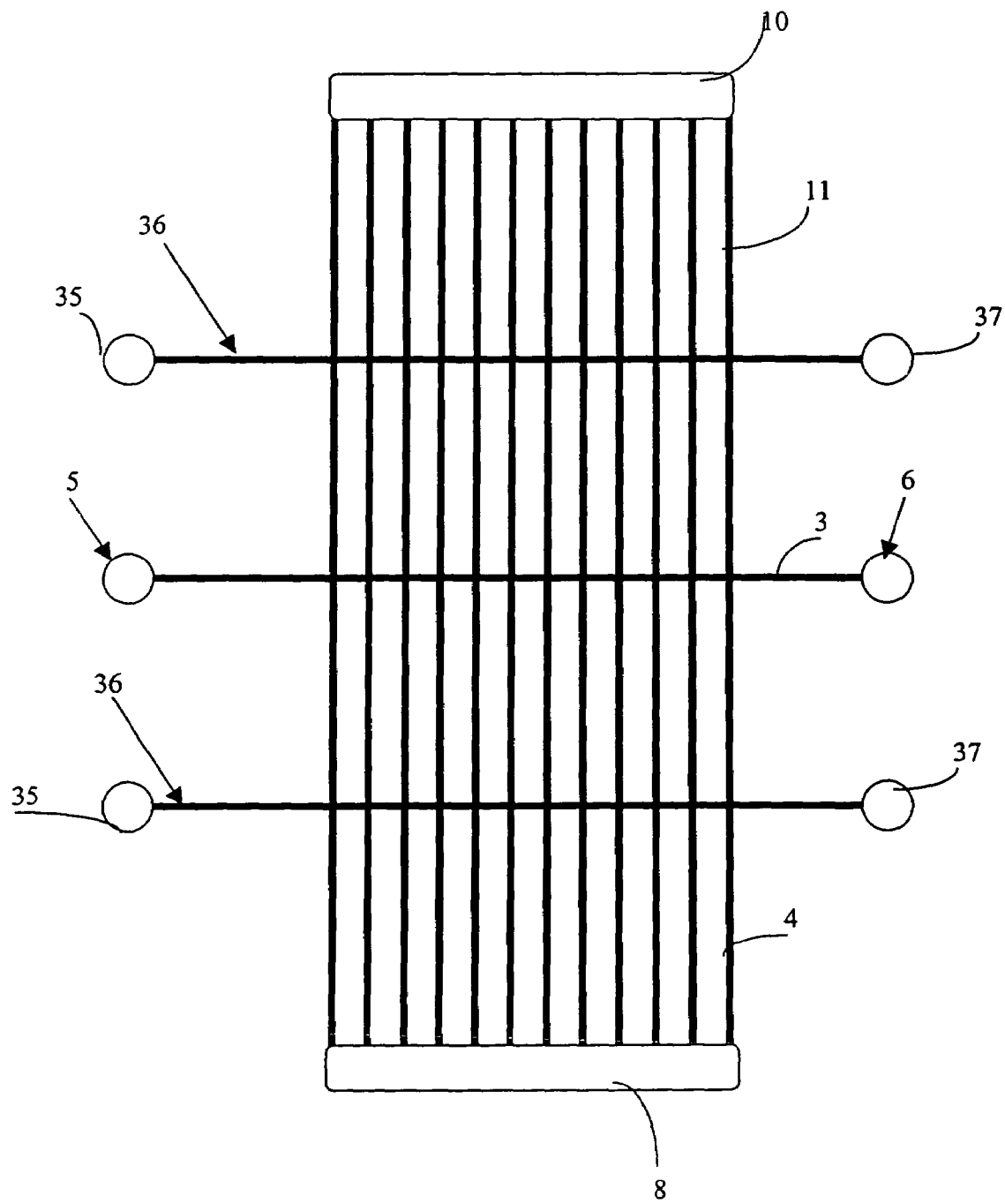
FIG. 6 is a schematic of a microfluidic apparatus with voltage control microchannels intersecting tertiary or second-dimension microchannels according to one embodiment of the invention.

According to another aspect of the invention, depicted in FIG. 6, one or more voltage control microchannels 36 may intersect the one or more tertiary microchannels 11, and one or more voltage control microchannels 36 may intersect the one or more second-dimension microchannels 4.

Figure 7:
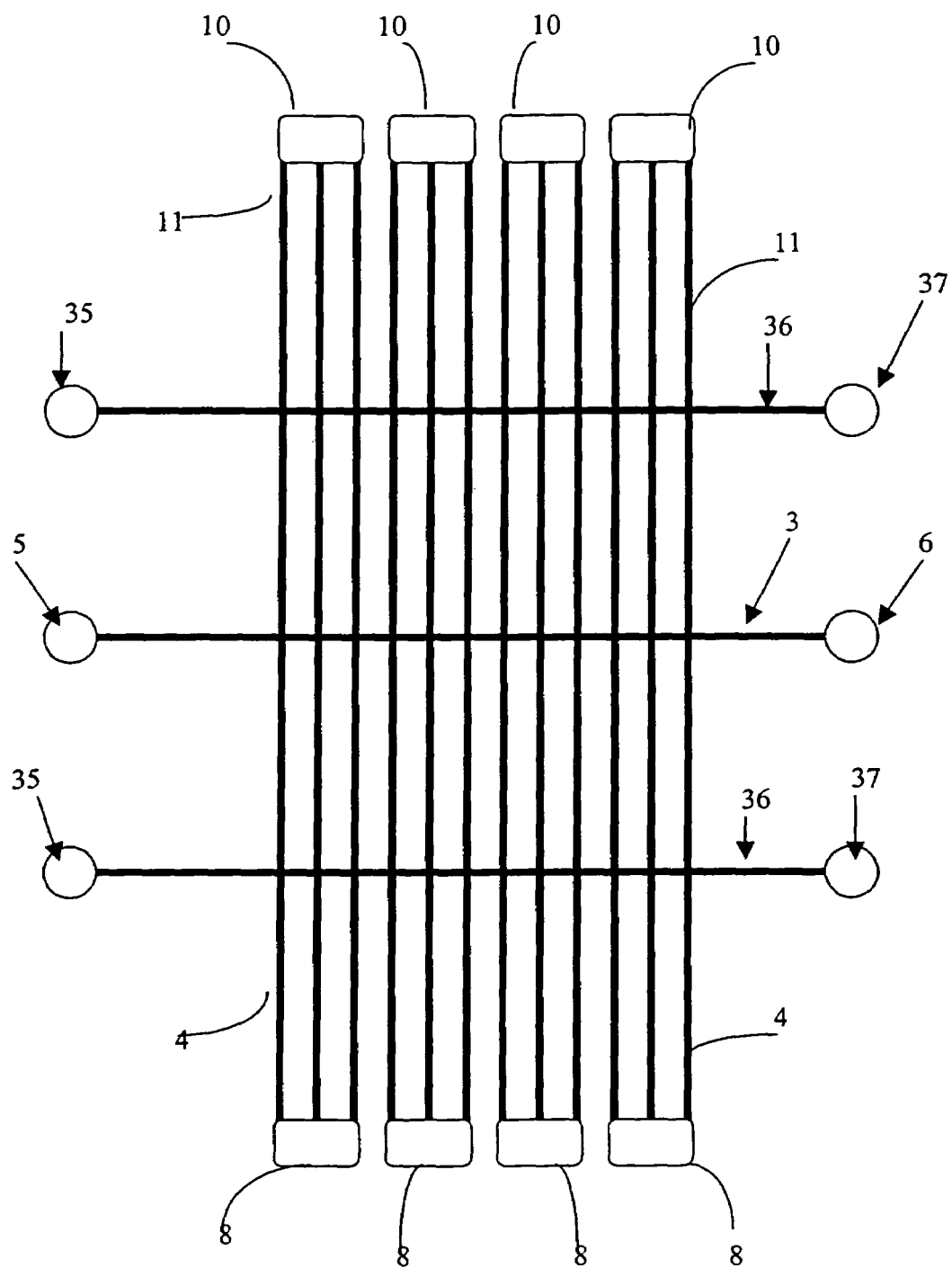
FIG. 7 is a schematic of a microfluidic apparatus with groups of tertiary or second-dimension microchannels according to one embodiment of the invention.

According to another aspect of the invention, depicted in FIG. 7, groups of one or more tertiary microchannels 11 may intersect one or more tertiary inlet reservoirs 10. Similarly, groups of one or more second-dimension microchannels 4 may intersect one or more second-dimension outlet reservoirs 8.

Figure 8:
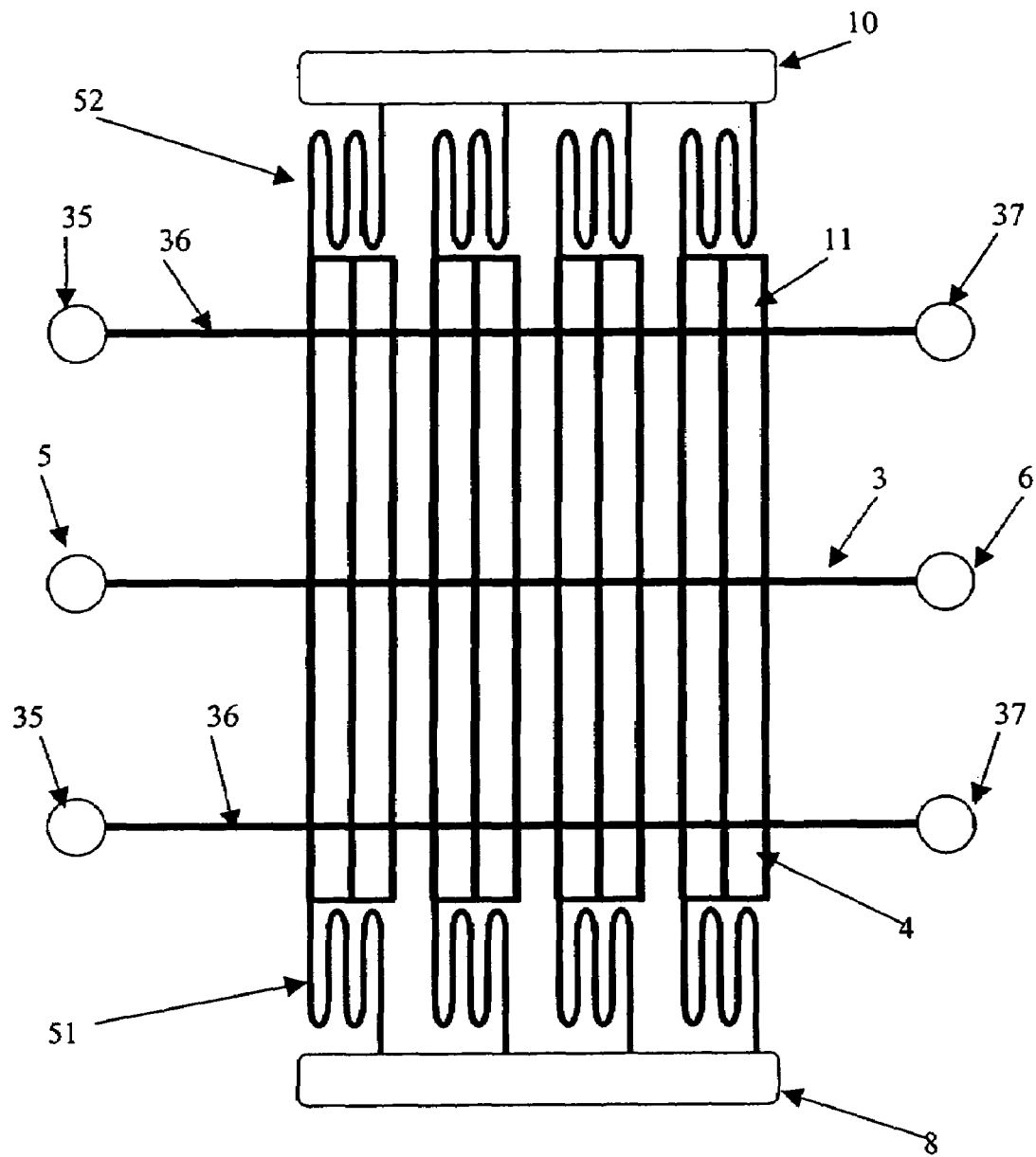
FIG. 8 is a schematic of a microfluidic apparatus with groups of tertiary or second-dimension microchannels merging into single common microchannels according to one embodiment of the invention.

According to another aspect of the invention, depicted in FIG. 8, groups of one or more tertiary microchannels 11 may merge into a single common tertiary microchannel 52, which intersects the one or more tertiary inlet reservoirs 10. Similarly, groups of one or more second-dimension microchannels 4 may merge into a single common second-dimension microchannel 51, which intersects the one or more second-dimension outlet reservoirs 8.

According to one embodiment, the one or more intersection control voltages may be applied using a plurality of voltage sources, wherein one voltage source may be connected to the first end of a first resistive element, and a second voltage source may be connected to the second end of the first resistive element to generate a potential gradient along the first resistive element. The resistive element may placed in electrical contact with the one or more second-dimension separation inlet reservoirs such that the intersection control voltage in each reservoir is set by the voltage of the first resistive element at the point of electrical contact. Further, the one or more intersection control voltages may be chosen such that the voltage near the intersection of the one or more first-dimension separation microchannels 3 and the one or more second-dimension separation microchannels 4 (connected to the reservoir at which the intersection control voltage is applied) is slightly different than the voltage within the intersection itself.

A third voltage source may be connected to the first end of a second resistive element, and a fourth voltage source may be connected to the second end of the second resistive element to generate a potential gradient along the second resistive element. The second resistive element may then be placed in electrical contact with the one or more second-dimension separation inlet reservoirs, such that the intersection control voltage in each reservoir is set by the voltage of the second resistive element at the point of electrical contact. The one or more intersection control voltages may be chosen such that the voltage near the intersection of the one or more first-dimension separation microchannels 3 and the one or more second-dimension separation microchannels 4 (connected to the reservoir at which the intersection control voltage is applied) is slightly lower than the voltage within the intersection itself.

Figure 9:
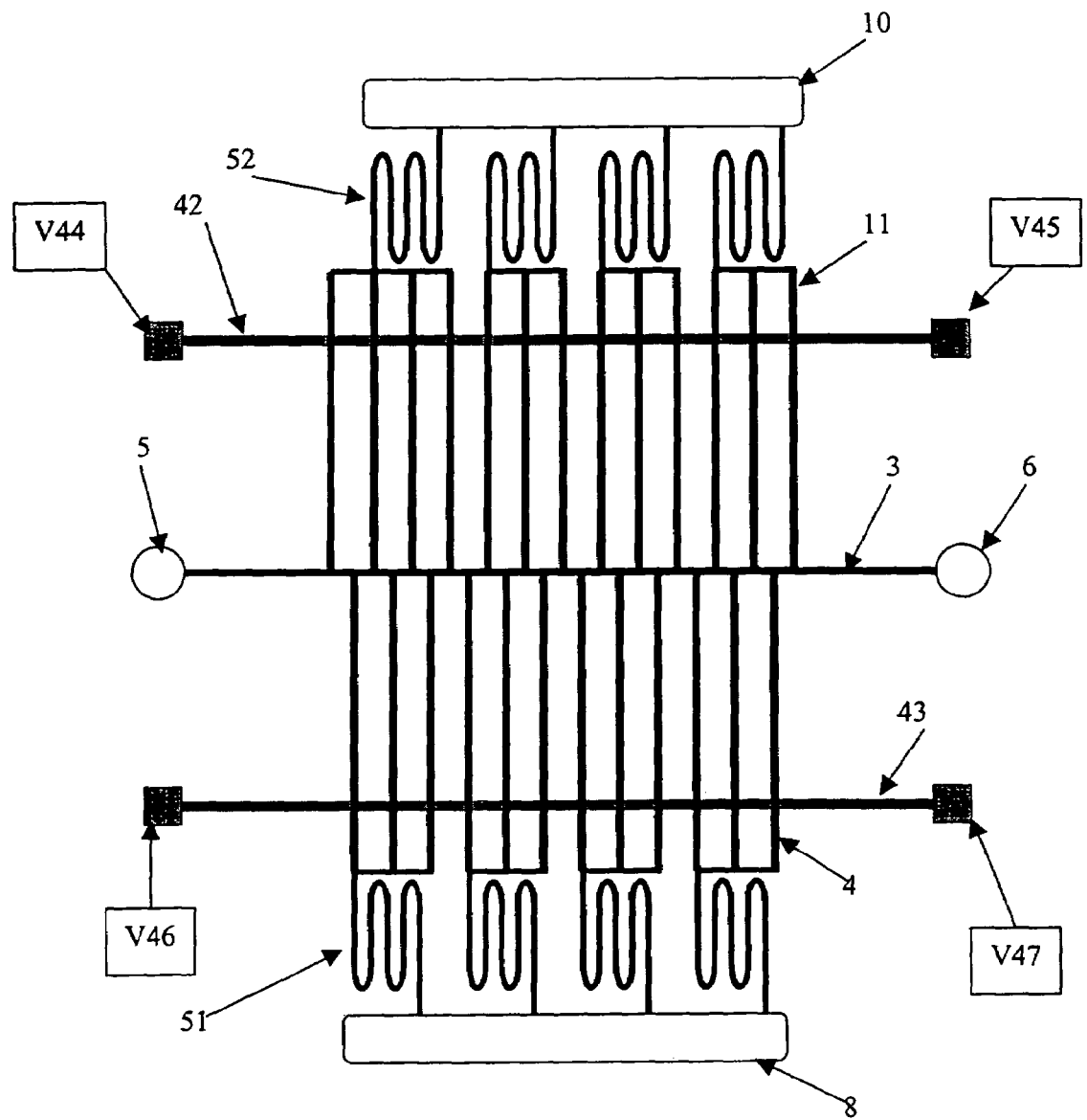
FIG. 9 is a schematic of a microfluidic apparatus with electrically resistive elements intersecting tertiary or second-dimension microchannels according to one embodiment of the invention.

According to another aspect of the invention, depicted in FIG. 9, one or more electrically-resistive elements (42, 43) such as a thin-film metal, wire, conductive polymer, or similar material may intersect the one or more tertiary microchannels 11 and the one or more second-dimension microchannels 4, with the one or more resistive elements (42, 43) in electrical contact with the fluid within the microchannels. One or more voltage sources (V44, V45, V46, V47) are applied at each end of the one or more resistive elements (42, 43), thereby creating a voltage drop along the length of the resistive elements (42, 43). Since the one or more resistive elements (42, 43) are in electrical contact with the fluid at the points of intersection with the microchannels, the local voltage at each point in the microchannel may be controlled in this manner, with the voltages defined by the one or more voltage sources (V44, V45, V46, V47) and the resistance of the one or more resistive elements (42, 43).

One of the advantages of the present invention is integration of a optical source device and an image capturing device for monitoring the detection of SDS-protein complexes near the end of second dimension microchannel array using noncovalent, environment-sensitive, fluorescent probes.

Figure 11:
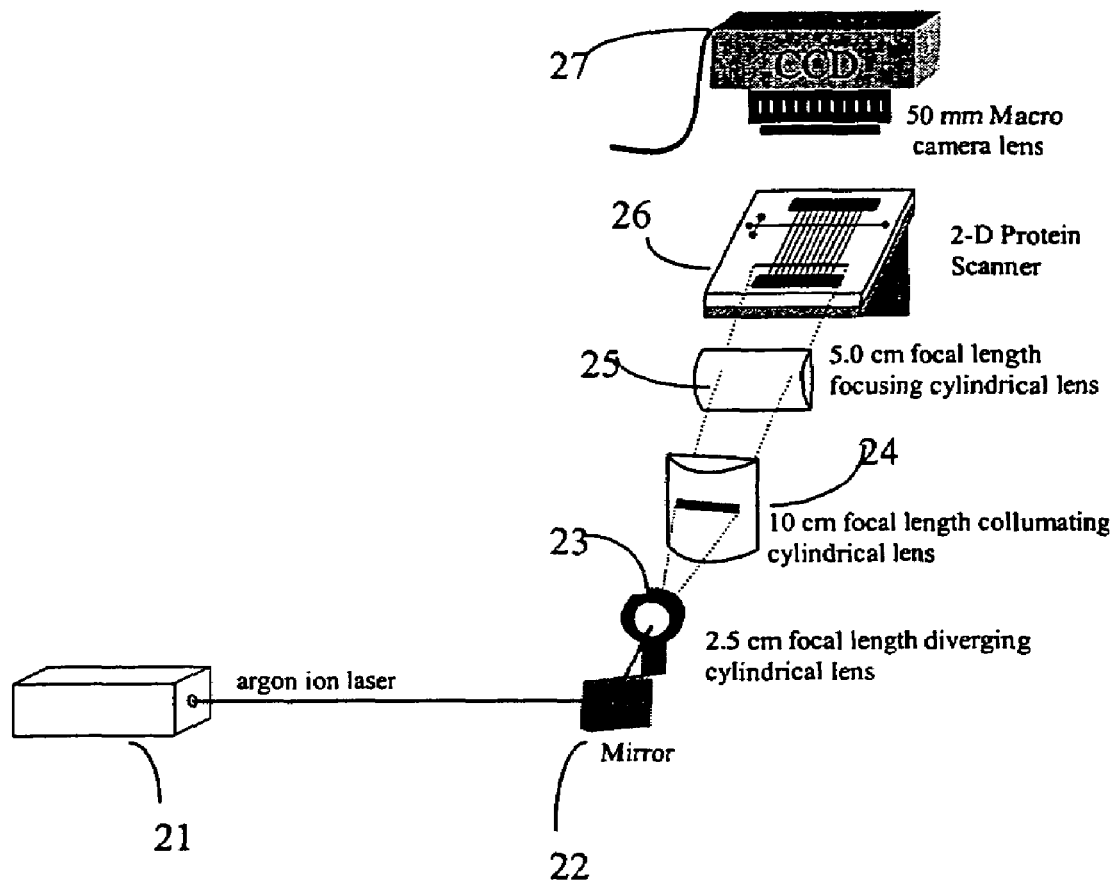
FIG. 11 is a schematic of laser-induced fluorescence detection setup for line-based fluorescence detection in second dimension of a microchannel array according to one embodiment of the invention.

For example, florescent probes such as SYPRO orange (excitation: 470 nm, emission: 570 nm) or SYPRO red (excitation: 550 nm, emission: 630 nm) may be employed for pre-electrophoretic staining of proteins. As shown in FIG. 11, an argon ion laser 21 may be used for excitation. The output beam from the laser is diverged, collimated to span the entire second dimension microchannel array, and focused vertically in a narrow line across the array. This is achieved using a (diverging) 2.5 cm focal length plano-concave cylindrical lens 23 in series with a (collimating) 10 cm focal length plano-convex cylindrical lens 24 and a (focusing) 5.0 cm focal length plano convex cylindrical lens 25, respectively. The fluorescence in each channel of the array is independently monitored using a charged-coupled device (CCD) camera 27 with a 50 mm macro Nikon camera lens. The CCD sensor is comprised of 26 μm pixels positioned in a 1024×128 array. The system is arranged so that a single column of pixels on the sensor is designated to measure the fluorescence intensity emitted from each individual channel over time. A holographic notch filter may be located in front of the image capturing device to filter out any laser scattering. It should be noted that any suitable detecting devices and image capturing devices known to one skilled in the art can be used with microfluidic 2-D PAGE system for monitoring the protein separations in the microchannel array.

According one aspect of the present invention, microfluidic 2-D PAGE may be integrated with mass spectrometry employing matrix-assisted laser desorption/ionization (MALDI) and electrospray ionization (ESI) for integrating protein separation, quantification, identification, and sequencing processes. Electrospray ionization may be integrated into the microfluidic network by extending the second-dimension microchannels to the outer edge of the device to form electrospray tips, or by combining traditional silica capillary electrospray tips into the microfluidic system. The integrated system offers large-scale analysis of proteins and "differential display" proteomics for comparisons of protein expression under various environmental and physiological conditions.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

We claim:

1. A microfluidic apparatus for performing two-dimensional bimolecular separations, the apparatus comprising:
   at least one first dimension microchannel having at least a first surface and a second surface;
   an array of second dimension microchannels intersecting the first surface of the at least one first dimension microchannel;
   an array of tertiary microchannels intersecting the second surface of the at least one first dimension microchannel;
   means for performing a first continuous separation in the at least one first dimension microchannel to produce a separated sample, wherein the first continuous separation includes isoelectric focusing;
   means for transferring the separated sample directly from the at least one first dimension microchannel to the second dimension microchannels; and
   means for introducing a first media in the at least one first dimension microchannel and a second media into the array of second dimension microchannels.

2. The apparatus of claim 1 wherein the means for introducing comprises pressure filling means.

3. The apparatus of claim 1 wherein the means for introducing is operable, prior to introducing a first media in the at least one first dimension microchannel, to fill the at least one first dimension microchannel and second dimension microchannels with a second media, electroosmotically remove the second media from one of the first dimension microchannel, and introducing a first media into the at least one first dimension microchannel.

4. The apparatus of claim 1 further comprising a hydrodynamic barrier between the at least one first dimension microchannel and second dimension microchannels to enable each to be filled with a different media.

5. The apparatus of claim 1, wherein the biomolecular separation is to be performed on a biomolecular material and the biomolecular material comprises protein.

6. The apparatus of claim 1 wherein the means for transferring the separated sample further comprises means for substantially retaining the first dimension separation upon transfer to the second dimension.

7. The apparatus of claim 1, wherein the first media comprises a media for isoelectric focusing in the first dimension, comprising carrier ampholytes for the creation of pH gradient in the first microchannel.

8. The apparatus of claim 1, wherein the second media comprises a media for size based separation of SDS-protein complexes in the second dimension based on their differences in electrophoretic mobility inside a polymer sieving matrix.

9. The apparatus of claim 1, wherein the first media is a sieving matrix selected from the group consisting of:
   cross-linked polyacrylamide, linear polyacrylamide, polydimethylamide, N-acrylamoniethoxyethanol, hydroxyethylcellulose [HEC], poly(ethylene glycol), poly(ethylene oxide) [PEO], poly(vinylpyrrolidone) [PVP], nonionic polymeric surfactants, or n-alkyl polyoxyethylene ethers.

10. The apparatus of claim 1, further comprising a detector placed near an end of the array of second-dimension separation microchannels for differential display of protein expressions.

11. The apparatus of claim 1, further comprising a detector capable of monitoring substantially all of the full length and breadth of the array of second-dimension separation microchannels for differential display of protein expressions.

12. The apparatus of claim 1, further comprising a detector to monitor the performance of isoelectric focusing in the at least one first dimension microchannel, wherein proteins may be covalently labeled with a suitable florescent dye and detected by a suitable florescence detector.

13. The apparatus of claim 1, further comprising a detector to monitor the performance of isoelectric focusing in first dimension microchannels, wherein proteins in a biomolecular sample may be covalently labeled with a suitable florescent dye and detected by a suitable florescence detector and the microchannels are formed from a substrate optically transparent at the wavelengths used for the fluorescence detection.

14. The apparatus of claim 1 further comprising an integrated optical detection system.

15. The apparatus of claim 1 further comprising an integrated laser-induced fluorescence detection system.

16. A microfluidic apparatus for performing two dimensional bio-molecular separations, the apparatus comprising:
   at least one first dimension microchannel having at least a first surface and a second surface;

an array of second dimension microchannels intersecting the first surface of the at least one first dimension microchannel;

an array of tertiary microchannels intersecting the second surface of the at least one first dimension microchannel;

means for performing a first biomolecular separation in the at least one first dimension microchannel to produce a separated sample, wherein the first biomolecular separation includes size-based separation;

means for transferring the separated sample to the microchannels of the array of second dimension microchannels; and means for performing a second separation in the second dimension microchannels, where the second separation is performed by applying a temperature gradient.

17. The apparatus of claim 16 wherein the biomolecular separation is performed on a biomolecular material and the biomolecular material comprises DNA.

18. A microfluidic apparatus for performing two-dimensional protein separations, the apparatus comprising:

at least one first dimension microchannel for performing a first protein separation, wherein the first protein separation includes isoelectric focusing;

an array of one or more second dimension microchannel for performing a second protein separation, wherein the second protein separation includes size-based separation;

an array of one or more tertiary microchannels;

one or more electrodes that intersect one of the one or more second dimension microchannels or the one or more tertiary microchannels; and one or more voltage sources operatively connected to the one or more electrodes to control the voltage at the points of intersection of the microchannels.

* * * * *